(12) United States Patent
Raghibizadeh et al.

(10) Patent No.: US 8,554,362 B2
(45) Date of Patent: Oct. 8, 2013

(54) APPARATUS FOR PROCESS AUTOMATION USING A PIN AND BUSHING ARRAY

(76) Inventors: Sasan Raghibizadeh, North York (CA); Charles Boone, Toronto (CA)

( * ) Notice: Subject to any disclaimer, the term of this patent is extended or adjusted under 35 U.S.C. 154(b) by 0 days.

(21) Appl. No.: 13/409,620

(22) Filed: Mar. 1, 2012

(65) Prior Publication Data

US 2012/0161377 A1 Jun. 28, 2012

Related U.S. Application Data

(62) Division of application No. 11/557,105, filed on Nov. 6, 2006, now Pat. No. 8,150,548.

(60) Provisional application No. 60/733,765, filed on Nov. 7, 2005.

(51) Int. Cl.
*G06F 7/00* (2006.01)

(52) U.S. Cl.
USPC .......................................................... 700/230

(58) Field of Classification Search
USPC ........... 700/213, 228; 414/2, 222.12, 222.02; 422/63
See application file for complete search history.

(56) References Cited

U.S. PATENT DOCUMENTS

| | | | | |
|---|---|---|---|---|
| 5,544,683 | A * | 8/1996 | Guhl | 141/65 |
| 6,024,925 | A * | 2/2000 | Little et al. | 422/507 |
| 6,409,925 | B1 * | 6/2002 | Gombinsky et al. | 210/695 |
| 2003/0027345 | A1 * | 2/2003 | Friswell et al. | 436/49 |
| 2004/0096367 | A1 * | 5/2004 | Schermer et al. | 422/100 |
| 2005/0245113 | A1 * | 11/2005 | DeSilva et al. | 439/140 |
| 2006/0269385 | A1 * | 11/2006 | Zobel et al. | 414/403 |
| 2009/0180931 | A1 * | 7/2009 | Silbert et al. | 422/63 |
| 2009/0257858 | A1 * | 10/2009 | Weclawski et al. | 414/749.1 |

* cited by examiner

*Primary Examiner* — Ramya Burgess
(74) *Attorney, Agent, or Firm* — Clark & Brody

(57) ABSTRACT

An apparatus comprises a plurality of bushings arranged and held together in an array; and a plurality of pins residing in the plurality of bushings, wherein the plurality of pins are for transferring samples. Manufacturing tolerances for inside diameters of the bushings and outside diameters of the pins substantially match to allowing the pins to slide freely within the bushings. The plurality of bushings can reside in one or more plates, each of which having plurality of holes, with the plurality of bushings being held together in the array.

4 Claims, 24 Drawing Sheets

APPARATUS FOR PROCESS AUTOMATION USING A PIN AND BUSHING ARRAY

CROSS REFERENCE TO RELATED APPLICATIONS

This application claims priority to U.S. Provisional Patent Application No. 60/733,765 filed on Nov. 7, 2005.

BACKGROUND

1. Field

This invention relates to the field of process automation devices, and, in particular, to automation devices used in processes to be performed on chemical, biochemical, or biological samples and specimens.

2. Related Art

The use of automation in laboratory environments and pharmaceutical, manufacturing, and packaging or similar industries is well known. In molecular biology laboratories, for example, automation is used to transfer, mix, store, detect and analyze biological samples such as DNA, proteins, cells, tissues or similar samples in a high-throughput manner. In pharmaceutical industries automation is commonly used, for example, for high-throughput screening of compound libraries for discovering a new drug. Such processes usually involve one or more work samples that must go through different operations. Typically, such a system consists of a plurality of devices each of which performs one or more operations on a work sample. In laboratory environments, typically, standard labware or containers are used to hold a plurality of work samples, and a robot or a conveyer is employed to transfer the labware or containers from one device to another. The process, which consists of a set of work samples and operations is usually defined by a process manager, and may need to be re-defined from time to time. Therefore, the majority of such systems include a Computer Processing Unit (CPU) with a software package, which offers a Graphical User Interface (GUI) to the process manager for defining a new process and for running, monitoring, and controlling a process on the said plurality of devices.

While there are currently a number of such process automation systems in the market, there are several drawbacks to such systems. The currently available systems typically consist of a plurality of standalone and specialized instruments, such as for example a liquid handling robot, incubators and plate stackers that are integrated using a control computer and software that communicates with all such devices and synchronizes their operation. The drawback of integrating such specialized instruments is usually an increased complexity, higher cost, and lack of enough flexibility and scalability. Another drawback is that such independent instruments do not fully utilize the vertical dimension, which eventually leads to an increased footprint of the system. Also, the current systems typically use a multi-degree of freedom robot or a conveyer belt to transfer the samples. Such transfer mechanisms normally lack the precision required for high-precision operations such as microarraying. Therefore, the work sample has to first be transferred to a precise holder before any operations can be performed upon. Lack of specialized tools such as for example a very high-density pinhead is another shortcoming.

Accordingly, it would be advantageous to build a complex process automation system from mostly identical simpler building blocks that could be rearranged and installed in different configurations and could be equipped with a plurality of tools. It would also be advantageous to effectively utilize the vertical space in order to minimize the footprint. Further, it would be advantageous to utilize a high-precision transfer device or conveyer to transfer work samples and at the same time locate the samples for high-precision operations.

SUMMARY

One object of the invention is to provide a process automation apparatus in which the core of the system is made of mostly similar building blocks, called functional modules. This provides a modular, reconfigurable, and fully scalable approach to automation of processes that are typically found in laboratory environments, pharmaceutical industries, and high-precision manufacturing lines. Such modularity and scalability can be implemented in hardware and software of the apparatus.

Another object of the invention is to provide a process automation apparatus that minimizes the overall footprint by effectively using the available vertical space (Z direction).

Another object of the invention is to provide a process automation apparatus in which one or more functional modules are arranged along a precise conveyer device such that the conveyer constitutes the X-axis for the functional modules. Therefore, a functional module needs to move the tool in only two directions of Y and Z in order to achieve the full functionality of a 3D X, Y, and Z gantry robot.

Another object of the invention is to provide specialized tools and sub-modules for the said process automation apparatus. That includes a very high-density pinhead tool, a re-arrayer pinhead tool and a wash tower sub-module.

Another object of the invention is to provide a process automation apparatus in which a computer having user interface elements such as display, keyboard, mouse, and control software is operably connected to the said plurality devices and tools. The control software provides a graphical user interface (GUI) for the user to define new processes or edit the existing ones, and it supports the reconfigurability and scalability features of the hardware.

BRIEF DESCRIPTION OF DRAWINGS

The invention is described by way of example only, with reference to the accompanying drawings, in which.

DETAILED DESCRIPTION

In the following description, for purposes of explanation, numerous specific details are set forth in order to provide a thorough understanding of the invention. It will be apparent, however, to one skilled in the art that the invention can be practiced without these specific details.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Figure 1:
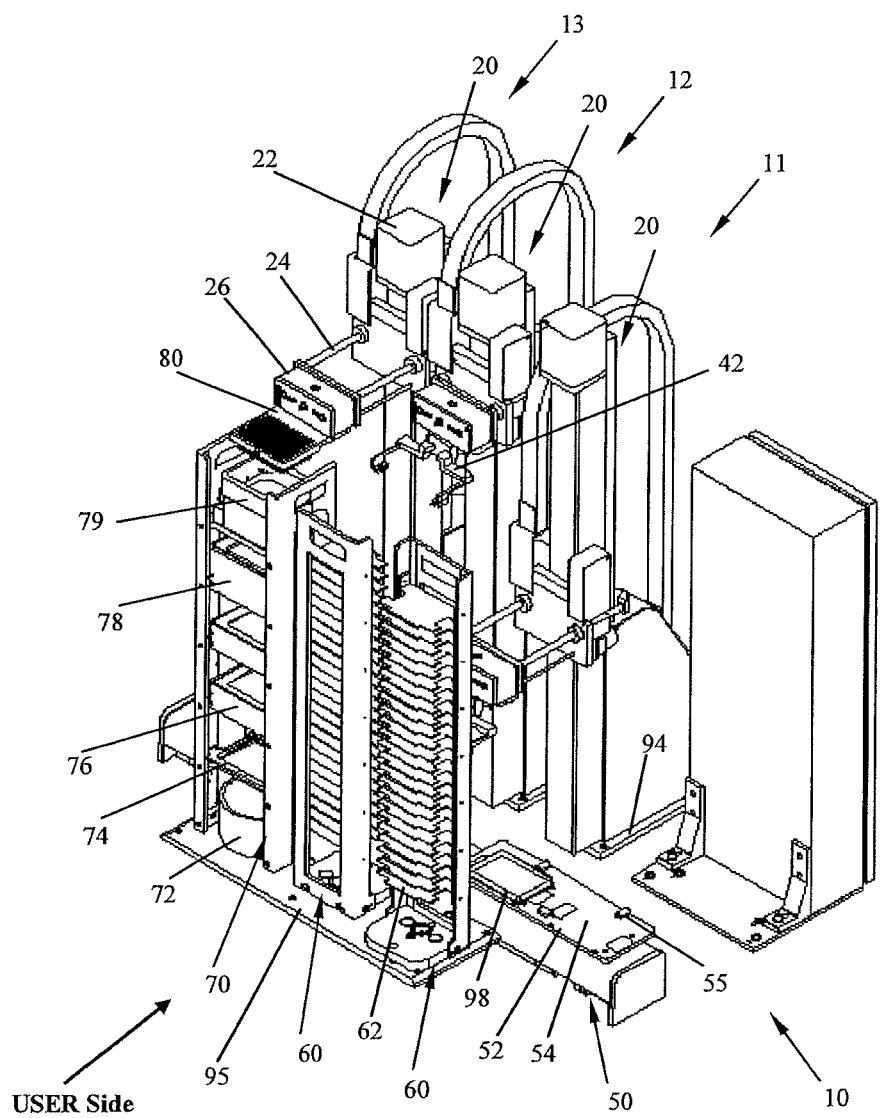
FIG. 1 is a perspective view of an exemplary configuration of the modular and scalable apparatus for automating a process in accordance with an embodiment of the present invention.

FIG. 1 illustrates an exemplary configuration 10 of a modular and scalable apparatus for process automation according to an embodiment of the present invention (hereinafter referred to as an automation system). The automation system 10 for example can be used for replicating or transferring an array of biological samples (e.g., Yeast cells) from one sample container to another one. It is to be understood that the automation systems disclosed herein are not limited to the configuration shown in FIG. 1. This will become more evident in subsequent parts of this document where other exemplary configurations of such a system are disclosed.

Figure 2:
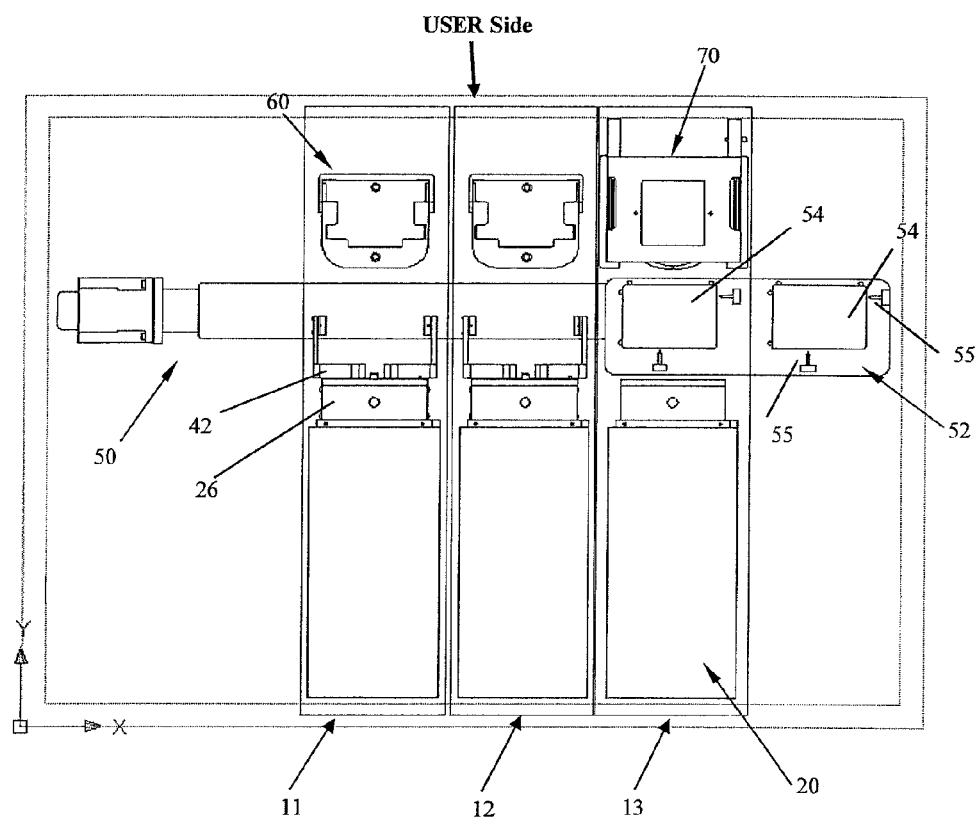
FIG. 2 is an illustration corresponding to FIG. 1, but showing a schematic top view of the exemplary configuration of the modular apparatus in accordance with an embodiment of the present invention.

FIG. 2 is an illustration corresponding to FIG. 1, but showing a schematic top view of the automation system 10, in accordance with an embodiment of the present invention. As illustrated in FIGS. 1 and 2, one embodiment of the process automation system 10 of the present invention comprises a plurality of functional modules 20, at least one conveyer 50, a plurality of tools 42 and 80, and sub-modules 60 and 70. The conveyer comprises a tray 52, which has one or more holders 54 for holding sample containers 98. The containers 98 are precisely locked in position using actuators 55 and are transferred from one functional module 20 or station to another one by the conveyer 50.

Figure 20:
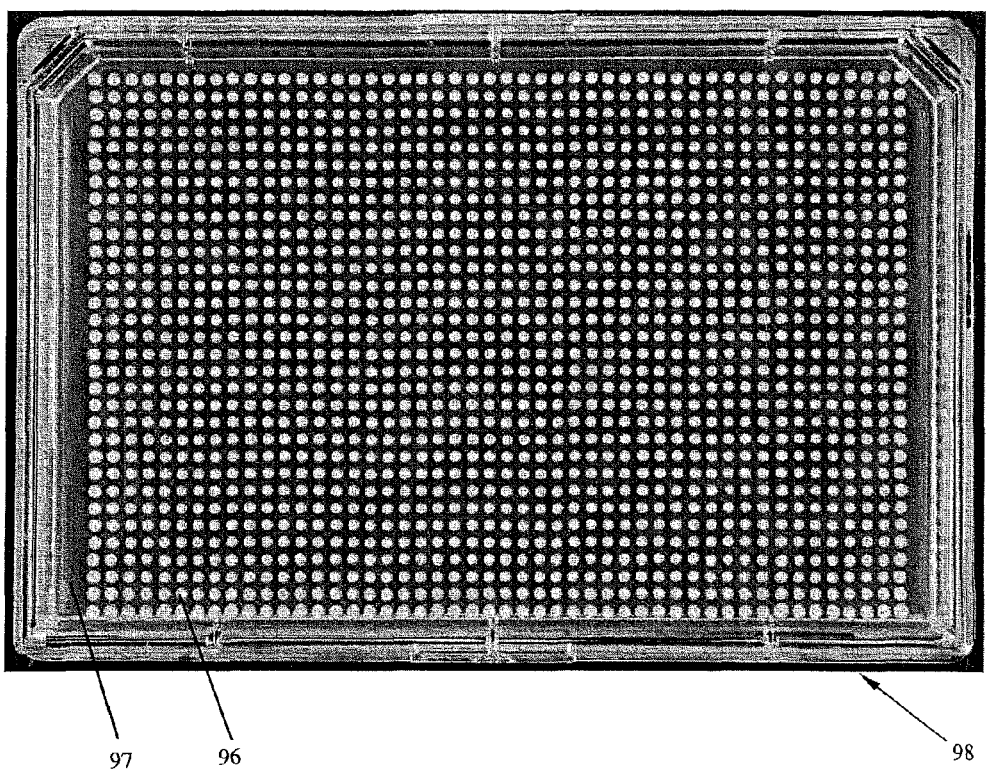
FIG. 20 illustrates a sample plate with 1536 different colonies of Yeast cells made by a 1536-pin replicating tool of FIG. 19D, in accordance with an embodiment of the present invention.

A functional module 20 comprises at least one general-purpose tool interface 26 and a device for moving the tool interface in space. In a preferred embodiment, a functional module 20 comprises a device 22 for moving in Z or vertical direction and a device 24 for moving in Y or horizontal direction towards the sub-modules 60 or 70. A typical process involves one or more work samples that have to go through a series of operations. Work samples can be any liquid solution or solid components and in one embodiment comprise biological, biochemical or chemical samples such as Yeast, bacteria or other types of cells, DNA, RNA or protein solution samples that are carried in one or more sample containers or labware 98. FIG. 20 shows an exemplary sample plate 98 that carries an array of 1536 different colonies of Yeast cells 96.

The cell colonies are grown on a proper growth media 97.

A functional module 20 performs at least one operation on work samples or sample containers. The operation of a functional module 20 is normally determined by the type of tool(s) and sub-module(s) that are operably connected to it. Such a combination of a functional module 20 and a tool(s) and sub-module(s) that are operably connected to it is hereinafter referred to as a machine For example, in FIG. 1 (from the right side) and FIG. 2 (from the left side), each of the first two functional modules 20 is equipped with a gripping tool 42 and a shelf sub-module 60. The third functional module 20 in FIG. 1 is equipped with a replicating tool 80 and a wash-tower sub-module 70. Therefore, there are three machines 11, 12, and 13 and one conveyer 50 in the exemplary automation system embodiment illustrated in FIG. 1 or 2. The first two machines 11 and 12 are hereinafter referred to as plate stackers and the third machine is hereinafter referred to as a plate replicator.

A plate stacker machine 11 or 12 comprises a functional module 20, a gripping tool 42, and a shelf sub-module 60. The shelf sub-module 60 comprises a plurality of shelves 62. A shelf is used to store a sample container (hereinafter also called a "plate" or a "micro-titer plate") 98 in a process. A gripping tool 42 is used by a functional module 20 to grip and transfer a plate from one location to another one, e.g., from a stacker shelf 62 to a conveyer holder 54, from one stacker shelf 62 to another stacker shelf 62, or from a conveyer holder 54 to a stacker shelf 62. A gripping tool 42 is also used to remove the lid of a sample container 98, to hold a lid or a container in space, or to put back the lid of a sample container 98.

A plate replicator machine 13 comprises a functional module 20, a replicating tool 80, and a wash-tower sub-module 70 as illustrated in FIG. 1 in accordance with an embodiment of the present invention. The machine is used to replicate or transfer an array of work samples such as Yeast cells from one sample container 98 to another one. It is also used to re-format the samples, for example re-formatting four 96-format arrays into one 384-format array of samples. The replicating tool 80 will be described in more detail in subsequent parts of the document. The wash-tower 70 is used to clean and sterilize the replicating tool 80 after a replication and also to pre-condition or pre-wet the tool before a replication. A wash-tower 70 comprises several units (hereinafter also called "modules" or "devices") 72, 74, 76, 78, and 79, wherein a module performs a specific cleaning or pre-conditioning operation. Such units of the wash-tower 70 will be described in more detail in subsequent parts of the document.

The abovementioned tools and sub-modules are only two examples of a group of tools and sub-modules that can be connected to a functional module 20 in order to create new machines in accordance with embodiments of the present invention. As should be obvious to one of ordinary skill in the art, an automation system embodiment of the present invention may suitably comprise other tools that are commonly used to automate laboratory processes, including but not limited to different formats of pipettors or liquid handling tools, bar-code readers, CCD (Charge Coupled Device) cameras, colony-picking tools, a magnetic pinhead, and microarraying print-heads. Similarly, by way of example and not limitation, a sub-module as disclosed herein may comprise a stacker shelf, a carousel, a stacker shelf within an incubator, a carousel with incubator, an incubator, a wash tower, a shaker, a centrifuge, a vacuum filteration manifold, a plate reader, a slide scanner, a gel reader, a magnetic stierer, a pierecer, a thermocycler, a plate reader, or a reagent library.

It is an advantageous aspect of automation system embodiments of the present invention that adding a new operation or functionality to the system is just a matter of replacing a tool and/or a sub-module. Also, it is to be appreciated that the number of functional modules 20 is not limited to three, and any number of them can be used to automate simpler or more complicated processes. This allows for said modularity, scalability, and reconfigurability of such an automation system.

In other words, the building blocks of such an automation system are the functional modules 20 and conveyer(s) 50. Functional modules are equipped with suitable tools and/or sub-modules to perform operations on work samples, and the conveyers are used to transfer the work samples among the functional modules. The functional modules and conveyers are operably connected to at least one controller (hereinafter also referred to as a central processing unit (CPU)) with a human-machine interface (HMI) using one or more communication links In one embodiment, one or more RS-232, RS-420, RS-485, universal serial bus (USB), or Ethernet links are used in order to exchange signals and commands The CPU can be a personal computer with 8086 types of processors or any other personal or mini-computer or mainframe. The CPU controls, synchronizes, and integrates the operation of the functional modules, conveyers, and their tools and sub-modules, and the HMI provides a Graphical User Interface (GUI) for a user to define and execute (or run) a desired laboratory or similar process.

Figure 3:
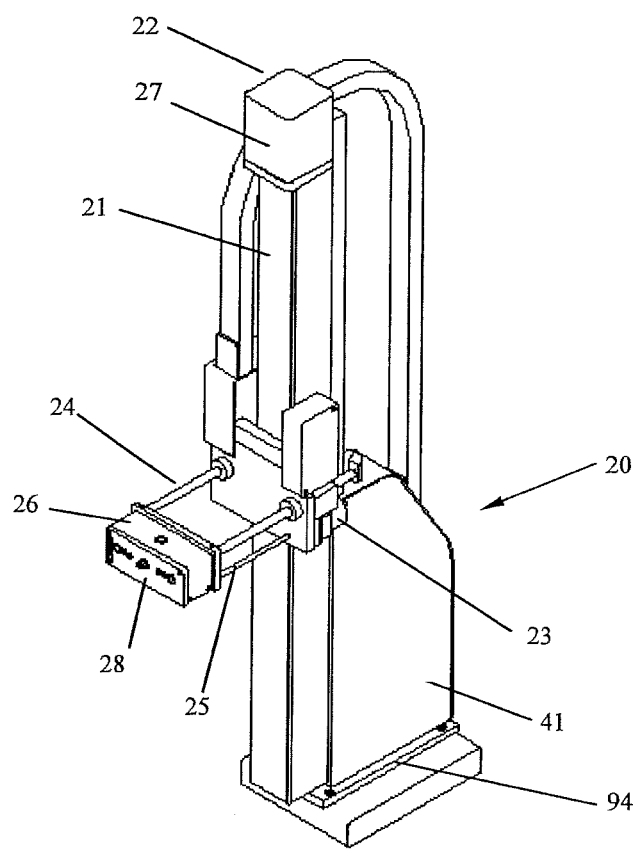
FIG. 3 is a perspective view of an example functional module used in the modular apparatus in accordance with an embodiment of the present invention.
Figures 4A, 4B, 4C:
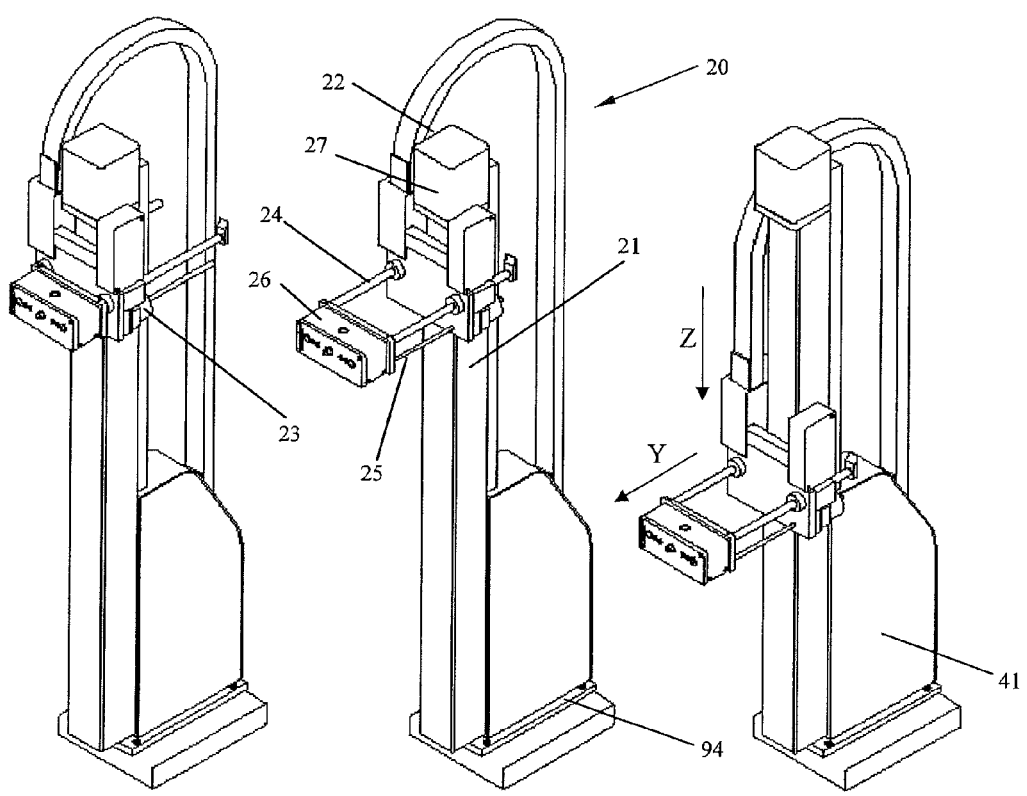
FIGS. 4A-4C correspond to FIG. 3, but show the movement of the general purpose tool interface of the present invention in Y and Z directions, in accordance with an embodiment of the present invention.
Figures 5A, 5B:
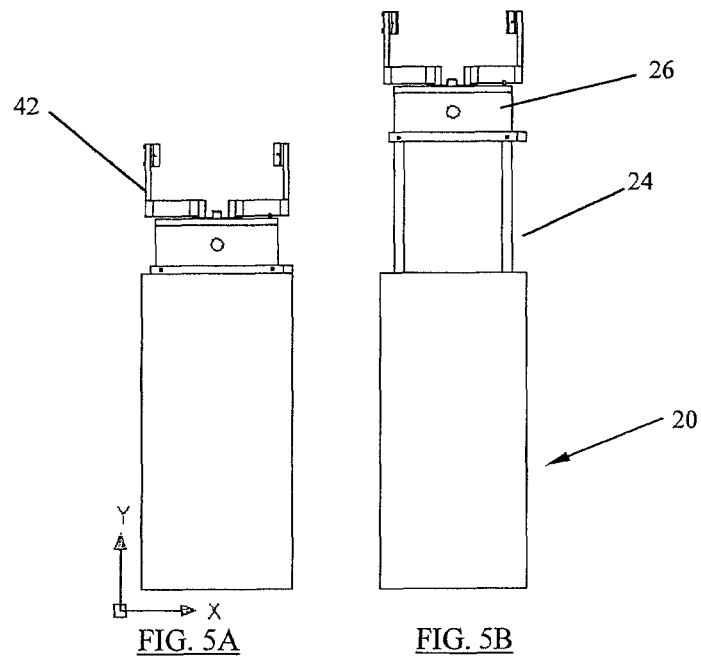
FIGS. 5A and 5B correspond to FIGS. 4A and 4B respectively, but show a schematic top view of the functional module and the movement of the tool interface in Y direction, in accordance with an embodiment of the present invention.

A functional module 20 comprises a general-purpose tool interface 26 that provides a unified way for attaching one or more different tools. A functional module further comprises one or more devices such as 22 and 24 that move the tool interface 26 in one or more desired directions in space. In one embodiment, a functional module moves the tool interface 26 in Z and Y directions, as illustrated in FIG. 4. FIG. 3 shows an exemplary embodiment of a functional module 20, in accordance with an embodiment of the present invention. The device 22 comprises a motor 27 and a linear actuator 21 that are used to move the tool interface 26 in vertical or Z direction. Similarly, the device 24 comprises a motor 23 and a linear actuator 25 that are used to move the tool interface 26 in horizontal direction Y. Such movements are illustrated in FIGS. 4 and 5. It is to be appreciated that a functional module may comprise other types or directions of movements for more complicated operations. In one embodiment, a functional module also comprises an enclosure 41 that contains the required electrical, pneumatic and hydraulic components of the module, and a fixed base 94 that defines the location and orientation of the functional module in relation to the other devices in the automation system.

Figure 6:
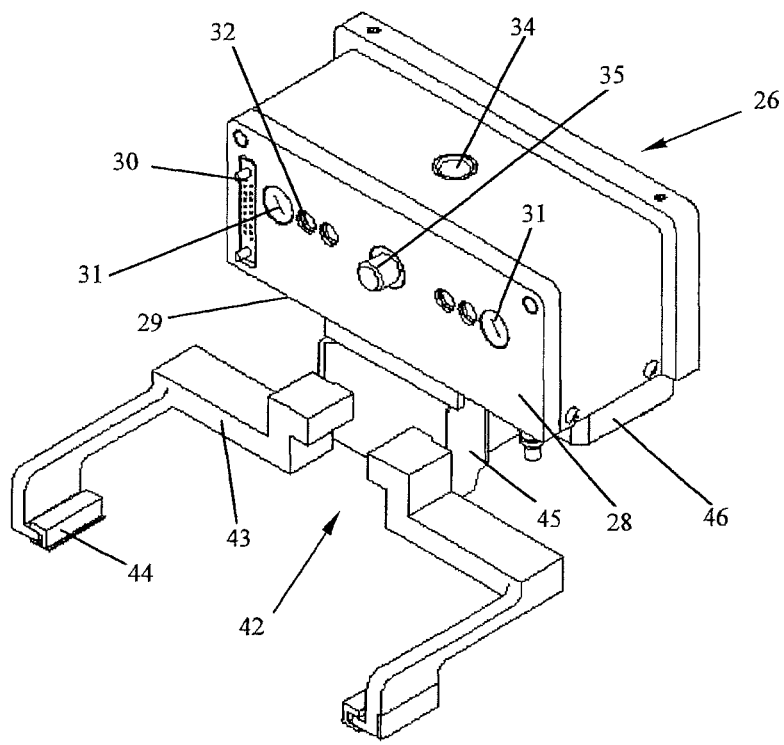
FIG. 6 is a perspective view of the tool interface and an exemplary gripping tool attached to the horizontal interface plane in accordance with an embodiment of the present invention.
Figure 7:
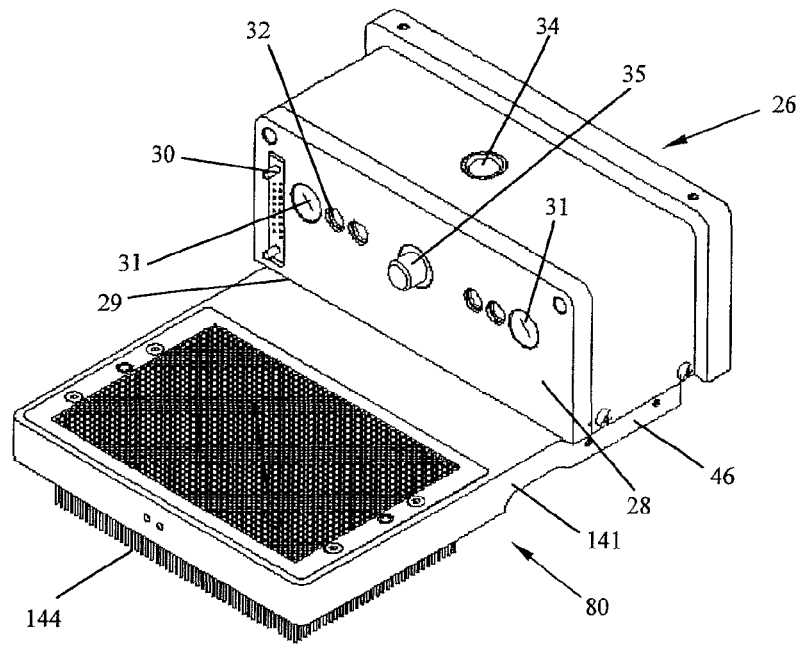
FIG. 7 is a perspective view of the tool interface and an exemplary pinhead tool attached to the horizontal interface plane in accordance with an embodiment of the present invention.

FIGS. 6 and 7 show the details of a general-purpose tool interface 26, in accordance with an embodiment of the present invention. Two exemplary tools, i.e. a gripper 42 and a replicator 80 are shown to demonstrate the function of the general-purpose tool interface 26. A general-purpose tool interface 26 comprises two interface planes: a vertical plane 28 and a horizontal plane 29. The two interface planes have similar features, therefore only the interface plane 28 is described here. Having two interface planes instead of one is a unique feature that provides more flexibility in attaching tools to a functional module. Some tools, e.g. a gripper 42 or a replicator 80, are more suitably attached to the horizontal interface plane 29 as shown in FIGS. 6 and 7, and some tools, e.g. a vertical CCD camera, are more suitably attached to a vertical interface plane, in accordance with embodiment of the present invention. More complicated tools may use both interface planes.

As illustrated in FIG. 6, an interface plane 28 comprises two accurate bushings 31 for precise mechanical registration of a tool with-respect-to the general-purpose tool interface 26, a screw mechanism 35 and an access hole 34 for attaching or detaching a tool, a plurality of pneumatic or hydraulic ports 32, and at least one electrical connector 30, in accordance with an embodiment of the present invention. A tool has an attachment site 46 that is complementary to a tool interface plane 28 or 29. This means that features on a tool interface plane 28 will suitably pair with corresponding features on a tool's attachment site 46. For example, a tool comprises a threaded hole that matches the screw 35 of the general-purpose tool interface plane 26, or pins that pair with the corresponding bushings 31 of the general-purpose tool interface 26, and so on. Such an arrangement allows for the electrical and pneumatic or hydraulic connections required for the operation of a tool to be provided after the tool is attached to the interface device 26.

Figure 17:
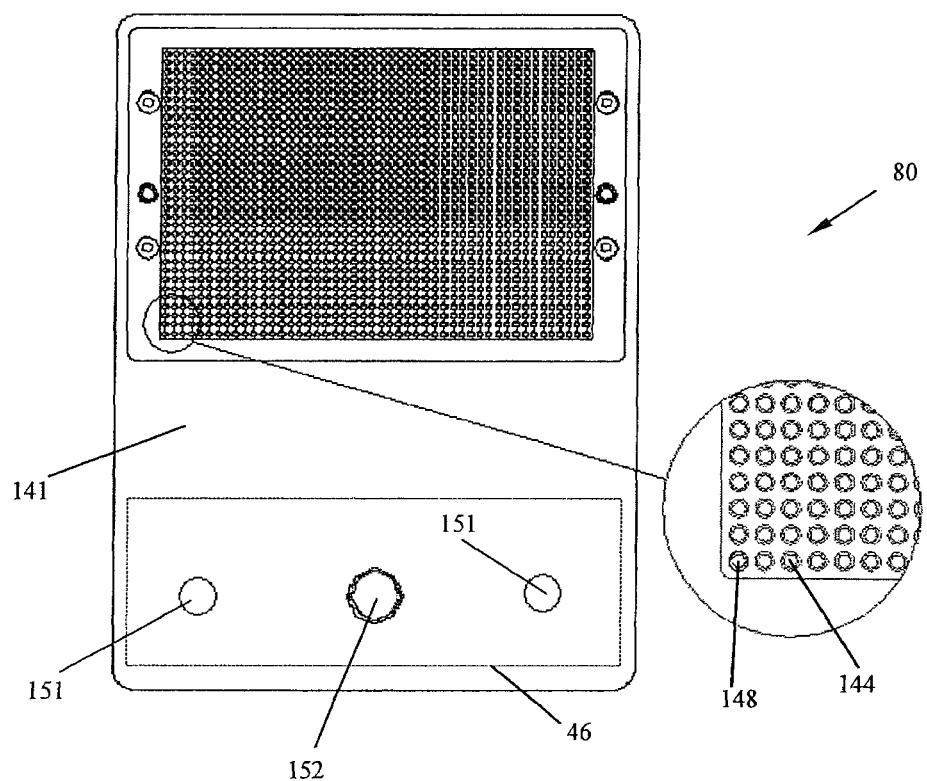
FIG. 17 is a top view of an example replicating pinhead tool of the modular apparatus of an embodiment of the present invention.

For example, in FIG. 6, the gripping tool 42 comprises an attachment site 46, a pneumatic actuator 45, two arms 43 with two jaws 44, and a switch that detects when the gripper is full or empty, in accordance with an embodiment of the present invention. One or more pneumatic lines required for the operation of the actuator 45, and electrical wires for the detection switch, are automatically connected when the tool 42 is attached to the general-purpose tool interface device 26. This provides a high level of modularity in which a tool can be easily exchanged in a matter of seconds. The tool exchange can be done manually or can be automated. FIG. 7 shows how a replicating tool is attached to the tool interface device 26, in accordance with an embodiment of the present invention. In this case, the replicating tool does not require any electrical, pneumatic, or hydraulic signals for its operation and only requires a mechanical attachment and a precise registration. FIG. 17 shows the top view of a replicating tool in which the attachment site 46 is illustrated as part of the base plate 141, in accordance with an embodiment of the present invention. Two mechanical pins 151 will pair with the bushings 31 of the tool interface plane 29 to provide a precise alignment of the tool after attachment. The mechanical attachment is achieved using a screw 35 on the bottom face 29 of the tool interface 26 and a threaded hole 152 on the tool 80. The access to the bottom screw 35 is obtained through an access hole 34 on top of the tool interface 26 shown in FIG. 7.

A typical operation cycle of the automation system 10 in FIG. 1 can be best described by way of example, according to an embodiment of the present invention. For purposes of exemplary illustration, consider that the user wants to replicate twenty sample containers 98 like the one shown in FIG. 20 (hereinafter referred to as source plates) onto twenty blank sample containers (hereinafter referred to as destination plates). The steps are as follows:

1. The user loads the shelves 62 of the first stacker machine 11 with twenty source plates and the shelves 62 of the second stacker machine 12 with twenty destination plates starting from the bottom shelf. To load the shelves 62, the user rotates the shelf sub-module 60 on the base 95 so that the shelves face the user side. This orientation is illustrated in FIG. 1 for the first stacker 11. The sub-module 60 can also be removed from the base 95, loaded outside, and put back on the base 95. Each shelf 62 holds one source plate 98. After loading all twenty plates, the user rotates the shelf sub-module 60 on the base 95 such that the shelves 62 face the functional module 20 (as illustrated in the second stacker machine 12).
2. The user runs a pre-defined procedure using the HMI of the CPU. A procedure defines the required steps for the system to complete a replication process.
3. Using the functional module 20 and the gripping tool 42, machine 11 picks up one source plate, and machine 12 picks up one destination plate from their corresponding shelves 62.
4. The conveyer 50 moves the tray 52 such that the right holder 54 stops in front of the functional module 20 of the first stacker 11. The distance between the functional modules 20 of the machines 11 and 12 is made equal to the distance between the two holders 54 of the tray 52. This allows that when the right holder 54 is in front of the functional module 20 of the first stacker 11, the left holder is in front of the functional module 20 of the second stacker 12.
5. The first stacker 11 puts the source plate on the right holder 54, and simultaneously the second stacker 12 puts the destination plate on the left holder 54. The plates 98 are locked in position using actuators 55.
6. The first stacker 11 picks up the lid of the source plate, and holds the lid in a safe position above the conveyer.
7. The conveyer moves the tray towards the replicating machine 13 along the X-axis such that the source plate is positioned accurately in front of the replicating machine 13 (see FIG. 2).
8. Referring to FIG. 20, the machine 13 picks up samples 96 from the container 98 using a replicating tool 80. Referring to FIG. 7, a replicating tool 80 comprises a plurality of pins 144, where each pin is used to pick up and replicate one sample 96 from the container 98. When a pin 144 dips into a cell colony 96, a large number of cells stick to the tip of the pin. If this pin touches the surface of a new or blank container, part of the cells are transferred (or replicated) onto the new surface. The result generally appears as a small spot on the new surface.
9. The conveyer moves the tray back to the original position such that the source plate is positioned in front of the first stacker 11.
10. The first stacker 11 puts back the lid of the source plate, and simultaneously, the second stacker 12 picks up the lid of the destination plate.
11. The conveyer moves the tray towards the replicating machine 13 along the X-axis such that the destination plate is positioned accurately in front of the replicating machine 13 (see FIG. 2).
12. The replicating machine 13 replicates the cells that stick to the pins 144 of the replicating tool 80 (see FIG. 7) onto the blank surface of the destination plate.
13. The conveyer moves the tray back to the original position such that the destination plate is positioned in front of the second stacker 12.
14. The second stacker 12 puts back the lid of the destination plate.
15. The replicating machine 13 starts sterilizing the pins 144 of the replicating tool 80 in the wash-tower sub-module 70. The sterilization process comprises several steps of washing followed by a drying step at the end in the dryer station 79. Washing steps comprise moving the replicating tool 80 to different wash stations 72, 76, and 78.
16. While the tool 80 is being washed, the stacker machines 11 and 12 pick up the first pair of source and destination plates 98 from the holders 54 (Note: the plates are unlocked by de-activating the actuators 55 before they can be picked up from the holders 54).

17. The first source and destination plates are put back on the shelves 62 and a new pair is removed from the shelves 62 and transferred to the conveyer holders 54.
18. After the wash cycle is completed, the replicating process is started from the step 6 above.
19. Such a cycle is repeated until all 20 pairs of source and destination palates are processed.

It is to be appreciated that the above procedure is used only to illustrate an operation cycle by way of example, and it will not limit the user from automating any other processes by defining a new set of tasks. The user of the system can define any number of procedures using the provided Graphical User Interface (GUI) and store them for later use.

Figure 11:
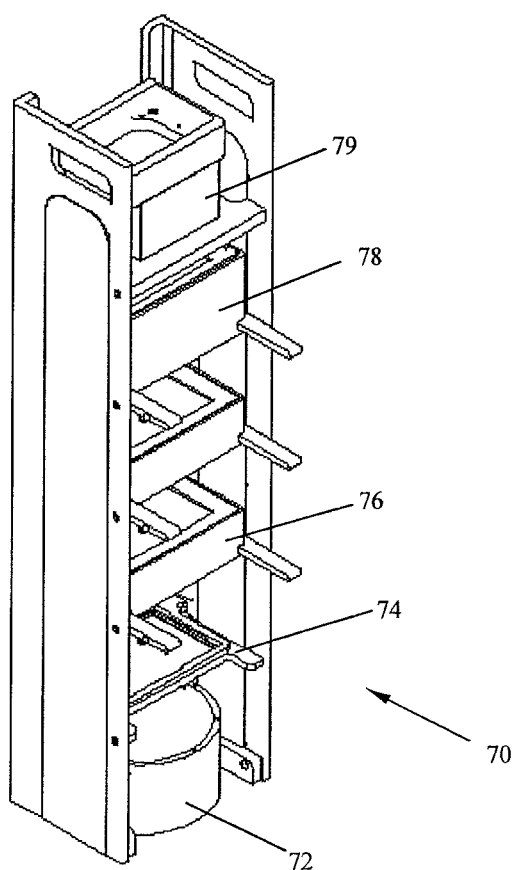
FIG. 11 is a perspective view of a wash tower sub-module of the modular apparatus of an embodiment of the present invention.
Figure 13:
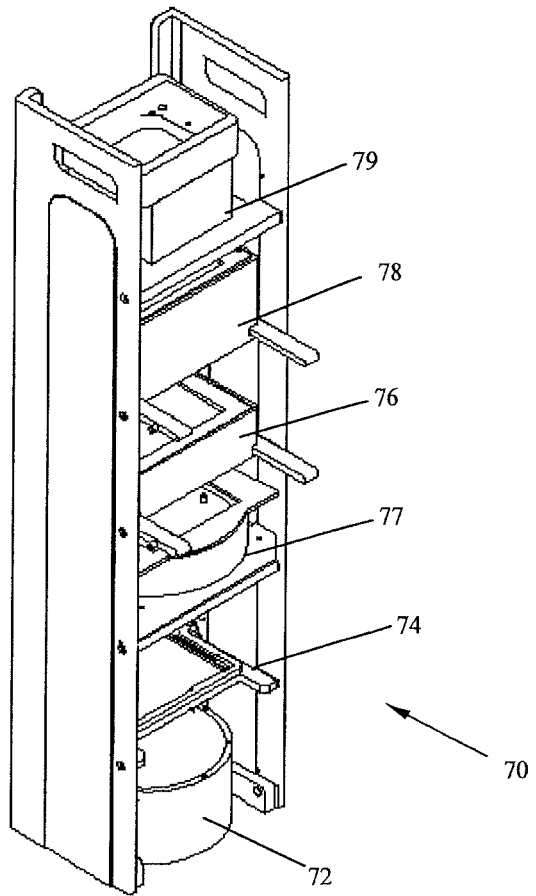
FIG. 13 is a perspective view corresponding to FIG. 11, but shows another arrangement of the wash stations in which a wash basin is replaced with circular brush station, in accordance with an embodiment of the present invention.

FIG. 11 shows a wash-tower sub-module 70, according to an embodiment of the present invention. As illustrated in FIG. 11, a wash-tower 70 comprises a plurality of devices that are arranged vertically and each device is used to perform an operation on the tool such as pre-conditioning, cleaning, or drying. It is to be appreciated that the wash-tower 70 in FIG. 11 is presented by way of example and the order, number, and type of devices in the wash-tower is not limited to the one shown in FIG. 11. For example, FIG. 13 shows another configuration of a wash-tower 70 in which the wash basin 76 is replaced with a circular brush station 77, in accordance with another embodiment of the present invention. A typical wash and sterilization operation involves several steps of cleaning in different solutions followed by a drying step. The number of cleaning steps and the type of solutions used in each step depend on the tool and work samples. For example, for a replicating tool 80 that uses an array of pins 144 (see FIG. 7) for transferring biological samples such as Yeast cells from one sample plate to another one, the following cleaning procedure can be used:

1. In a first step, the pins are dipped for about thirty seconds or more in the circular wash station 72 which is filled with distilled and de-ionized water. At this step, most contaminants such as Yeast cells tend to separate from the pins and float or subside at the bottom of the wash station. As will be illustrated later, the circular wash station is designed to completely drain, rinse and refill the wash station automatically after one wash or after every few washes. This helps reduce the likelihood of cross-contamination between the washes. Optionally, a wash station may be oval instead of circular.
2. In a second step, the pins are cleaned in an ultrasonic cleaner 78, which is filled with water or diluted ethanol. The ultrasonic cleaner comprises a metal tank filled with a wash solution and an ultrasonic transducer that induces high-frequency waves inside the solution. The waves generate dynamic forces that separate contaminants from the pins.
3. After cleaning in the ultrasonic cleaner 78, the pins are dipped in the wash basin 76, which is filled with diluted ethanol or another disinfectant.
4. In a forth step, the pins are dipped in the second wash basin 76, which is filled with 90% ethanol or similar solution. This step is generally the last step of sterilization and the first step of drying, as the 90% ethanol evaporates and dries quickly in air.
5. The dryer 79 then dries the pins by blowing warm air from the top.

After sterilization, the tool is ready for replicating another set of work samples. A pre-conditioning step might be needed in some cases. For example, it is observed that before replicating some biological samples such as Yeast cells, it would be advantageous to pre-wet the pins in distilled water. A pre-wetting station 74 is used for this purpose. This station comprises a container with a lid, and a lid-lifting mechanism. The lid is removed automatically for pre-wetting the tool, and after pre-wetting, it will be put back on the container to prevent contamination of the pre-wetting solution.

Figure 12:
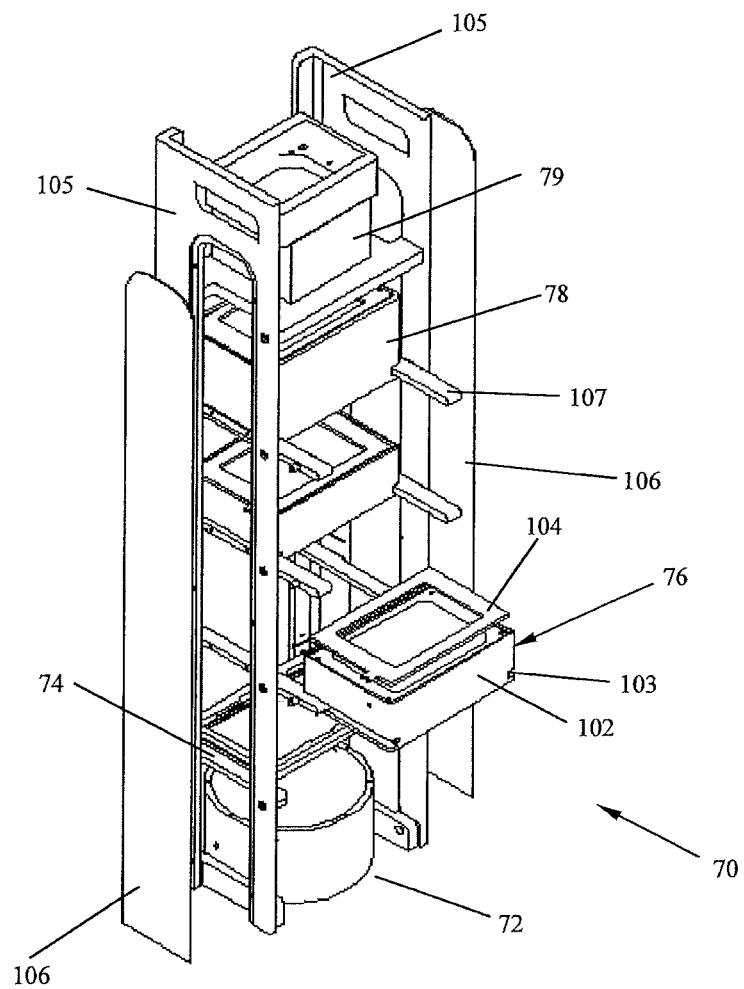
FIG. 12 is a perspective view corresponding to FIG. 11, but shows the assembly of side panels and a wash basin, in accordance with an embodiment of the present invention.

FIG. 12 shows an exemplary design of a wash-tower 70 with the main components and their assembly, in accordance with an embodiment of the present invention. The two side parts 105 constitute the main structure. The side covers 106 cover the longitudinal openings of the side parts 105. Such openings are used to run liquid and gas tubes and electrical wires to the devices at different levels. By removing the side covers 106 one can access the electrical wires or tubes. In one embodiment, one side opening is used for running electrical wires and the other one is used for running tubes. Some devices, such as wash basin 76 and the ultrasonic cleaner 78 are mounted on shelves 107 such that they can slide out horizontally or completely removed (as shown in FIG. 12 for the wash basin 76) for manual draining, cleaning, or refilling after completing a process.

As it is shown in FIG. 12, a wash basin 76 comprises a top frame 104 and a wash container 102 that can slide on shelves 107 using the side slots 103. The top frame 104 prevents the liquid to splash out when the basin is filled and manually moved back to the original position shown in FIG. 11.

FIG. 13 shows another configuration of a wash-tower sub-module 70, in which the first wash basin 76 in FIG. 11 is replaced with a circular brush station 77 (see FIG. 16 for details) for efficient cleaning of sticky samples, in accordance with an embodiment of the present invention. In this configuration, after the first step of cleaning in the circular wash station 72, the pins are cleaned in a circular brush station 77 filled with diluted ethanol or other sterilization solutions, followed by the ultrasonic cleaner 78, wash basin 76 with 90% ethanol, and the dryer 79.

An optional embodiment of the automation system, specialized for pre-conditioning, cleaning, or drying, comprises a wash-tower sub-module 70 and a functional module 20, but no conveyer 50. An advantage of such an embodiment is that it takes advantage of vertical space and minimizes the footprint of the specialized automation system.

Figure 16:
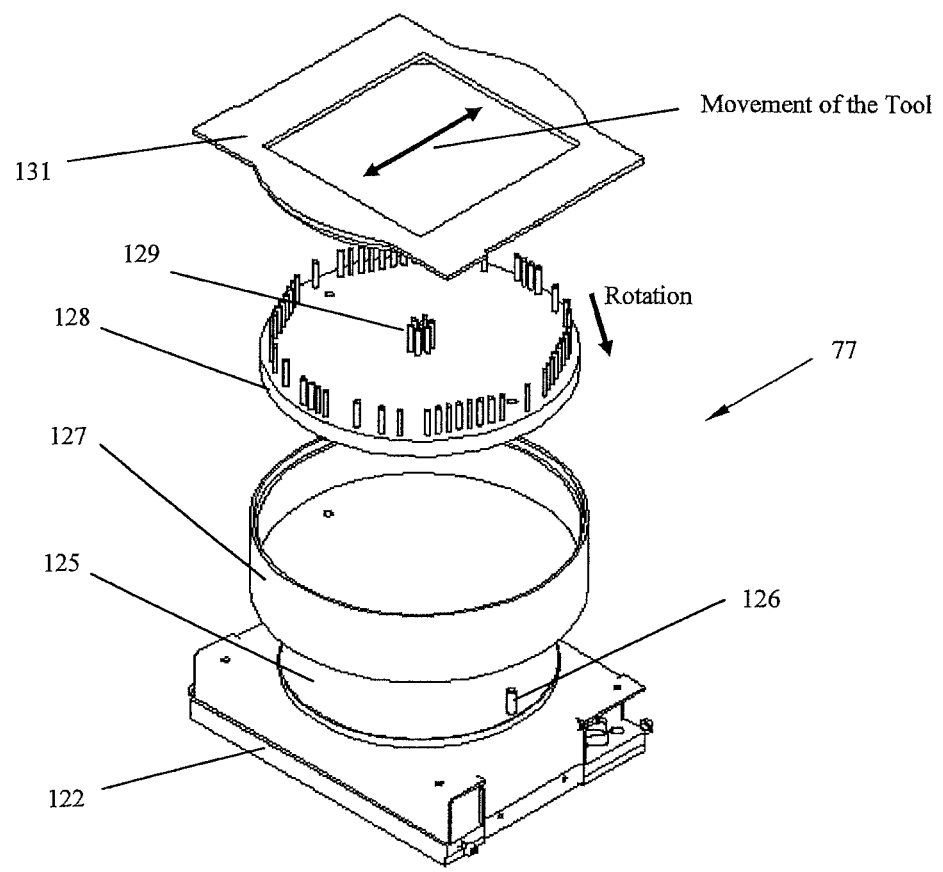
FIG. 16 is a perspective view showing the components and assembly of a circular brush station, in accordance with an embodiment of the present invention.

FIG. 16 shows the components and assembly of a circular brush station 77, in accordance with an embodiment of the present invention. The base plate 122 is used to mount the circular brush station 77 on the wash-tower 70 (see FIG. 13). In one embodiment, the base plate 122 is attached to the side parts 105 (see FIG. 12) using screws. As is shown in FIG. 16, the circular brush station 77 comprises a rotating mechanism 125, a container 127, and a circular brush 128 and 129. In one embodiment, a top cover 131 may be used to minimize splashing. The rotating mechanism 125 rotates around its central shaft using for example an electrical DC motor and a gear head (not shown in FIG. 16). The gear head reduces the rotation speed to few revolutions per second and amplifies the motor torque. The container 127 contains the wash solution and the circular brush 128 and 129. The circular brush comprises brushes 129 (only a few brushes are shown in FIG. 16) that are permanently attached to a base 128 such that they become one component. The wash container 127 sits on the rotating mechanism 125 and rotates with the mechanism 125 using two pins 126. The wash container 127 can be easily removed for manual draining, cleaning, and refilling of the container and the brush. In an embodiment of the present invention, a user lifts and removes the top cover 131, followed by lifting and removing the circular container 127 with the brush 128 and 129. Then, if needed, the user drains and cleans the container 127 and the brush 128 and 129. The brush is placed back into the container, and the container 127 is filled with a proper wash solution. Then, the filled container 127 is put back on the rotating disc 125, followed by putting back the top cover 131 on the container 127. The top cover 131 is an optional element that freely sits on the top edge of the container 127 and is positioned between the two side parts 105 of the wash-tower 70 (see FIG. 12). The two side parts 105 prevent the top cover 131 from rotating with the container 127. The main function of the top cover 131 is to prevent the liquid from splashing out during the operation.

During the operation of the device 77, the rotating mechanism 125, container 127, and circular brush 128 and 129 rotate together as shown in FIG. 16, in accordance with an embodiment of the present invention. While the brush 129 is rotating, the replicating tool 80 moves back and forth inside the rectangular window of the top cover in the direction shown in FIG. 16. The cleaning action happens when the tips of the pins 144 of the tool 80 (see FIG. 7) are in touch with the rotating brush 129. By moving the tool 80 back and forth, the pins, including the ones that are closer to the center of rotation, are cleaned properly and uniformly.

Figure 14:
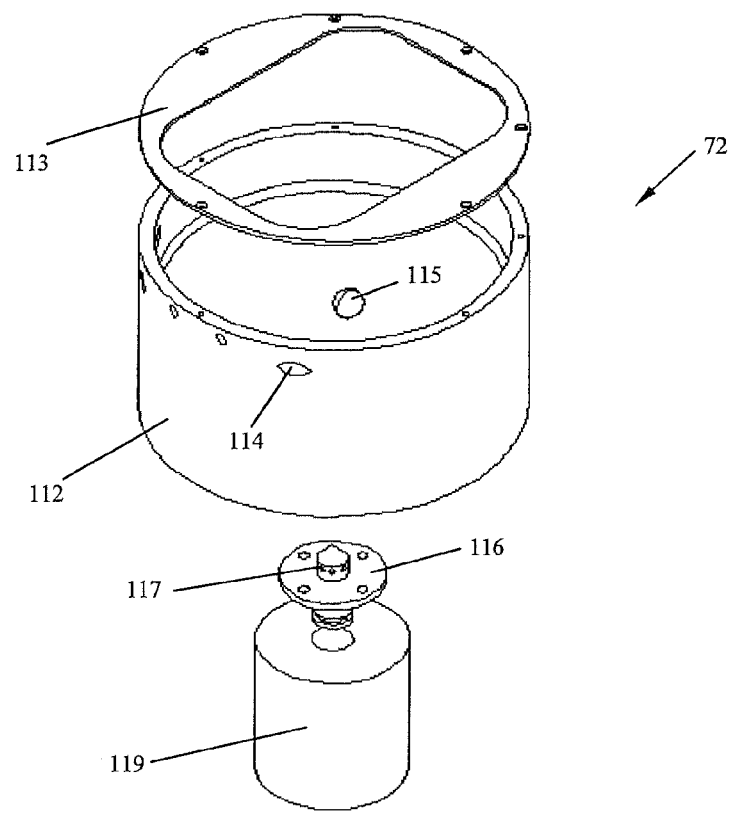
FIG. 14 is a perspective view showing the components and assembly of a circular wash station, in accordance with an embodiment of the present invention.
Figure 15:
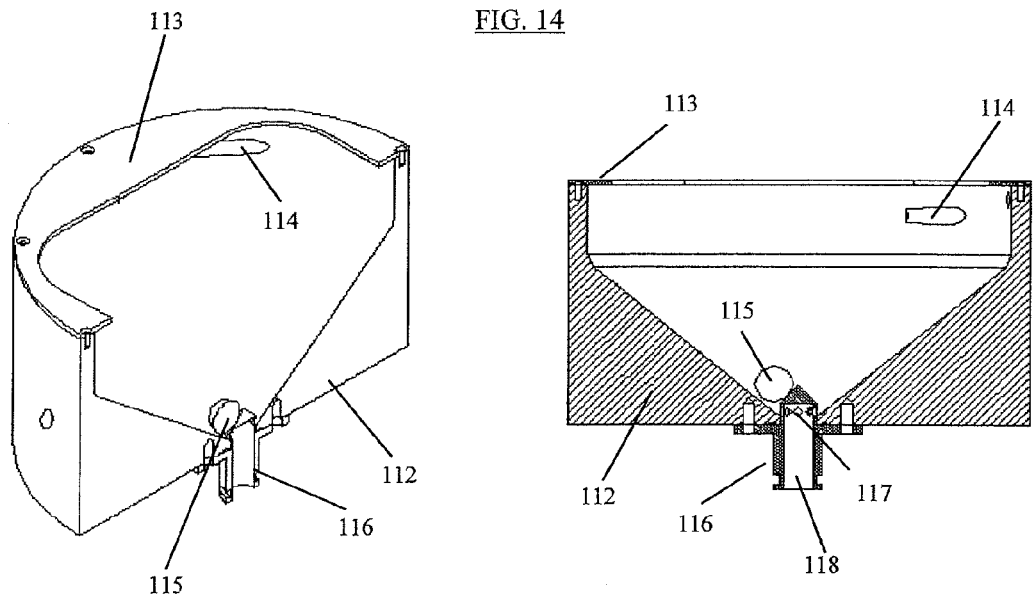
FIG. 15 corresponds to FIG. 14, but shows cross-sectional views of a circular wash station assembly, in accordance with an embodiment of the present invention.

FIG. 14 shows the components and the assembly of a circular wash station 72, in accordance with an embodiment of the present invention. It comprises a circular or oval container 112, a top cover 113, a centerpiece 116, a drain valve 119, and a metal ball 115. The cross-section of the container is shown in FIG. 15. The container 112 has one or more side holes or ports 114. In one embodiment, two side holes 114 (approximately 180° apart) are used. Through each side hole 114, one tube is inserted into the container 112 tangent to the inside wall. The inserted tube(s) is used to pump a cleaning solution into the container 112. The liquid enters the container 112 near the top and tangent to the inside wall (see the cross section in FIG. 15). The liquid then follows a spiral path to the bottom of the container 112 towards the centerpiece 116, creating a whirlpool. The liquid is drained through the side holes 117 and the exit port 118 of the centerpiece 116, when the valve 119 is open. To improve the draining efficiency, vacuum is used to suck the liquid from the bottom of the valve 119. The design of the centerpiece 116 and the existence of the metal ball 115 increase the efficiency of the suction. For example, if the centerpiece 116 and the metal ball 115 were not used and the liquid was drained directly through a centre hole, it would mostly drain air rather than liquid because the eye of the whirlpool would be located at that centre of the exit port. Therefore, instead of draining the liquid directly from the centre, the embodiment blocks the centre and uses the side holes 115 to drain the liquid. The metal ball 115 is used to break the symmetry of the whirlpool at the centre and improve the drain efficiency. Optionally, other obstacles, such as a dowel pin attached to the container near the centre, can be used instead of a ball for breaking the symmetry. But, the metal ball has the advantages of simplicity, cost, and performance. When the container 112 is being rinsed, the metal ball 115 slowly rolls inside the container and its own surface will get cleaned as well.

A typical operation cycle of a circular wash station 72, in accordance with an embodiment of the present invention, is as follows:

1. Fill operation:

To fill the container 112, the drain valve 119 is closed, and the wash solution is pumped through the ports 114, preferably with a slow speed in order to avoid creating a whirlpool. Optionally, another input port is used for filling the container.

2. When the wash station is used several times, the wash solution is generally contaminated and needs to be replaced. The container needs to be drained, rinsed, and refilled.

3. Drain operation:

The drain valve 119 is opened, and the contaminated solution is drained through the bottom hole 118 into a waste bottle. For faster draining, vacuum is applied to the waste bottle.

4. Rinse operation:

While the drain valve 119 is open and vacuum is applied to the waste bottle, wash solution is pumped into the container 112 through the input port(s) 114 with high speed. Simultaneously, the input water is drained from the bottom port 118. The input water creates a whirlpool that cleans the internal surface of the container 112, and the surfaces of the metal ball 115 and centerpiece 116.

5. Refill operation:

This operation is identical to the fill operation above.

FIG. 17 shows the top view of a replicating pinhead tool 80 (hereinafter also referred to as a "pinhead"), in accordance with an embodiment of the present invention. The tool 80 has an attachment site 46, which has two pins 151 and a threaded hole 152 for attaching the tool to the general-purpose tool interface 26 (see FIG. 7). A replicating tool 80 comprises a plurality of pins 144 that are arranged in specific formats, for example in a standard rectangular-array format such as a 96-format, 384-format, 768-format, or 1536-format as shown in FIGS. 19A, 19B, 19C, and 19D respectively, in accordance with embodiments of the present invention.

Figure 18:
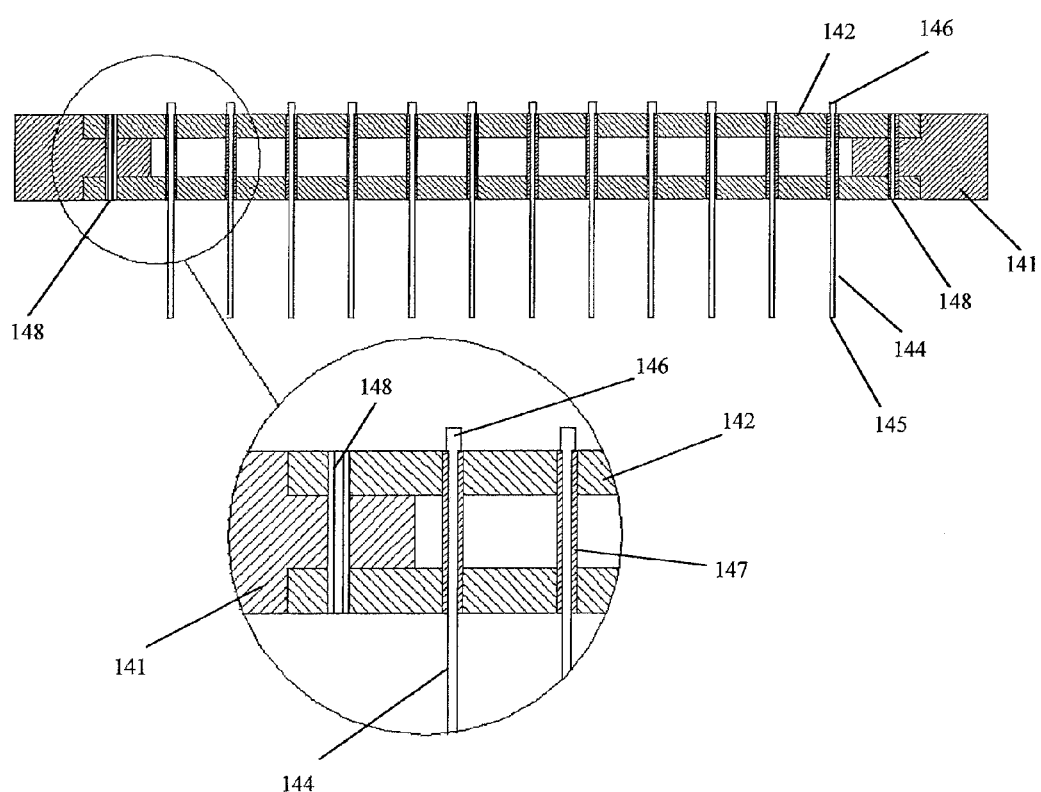
FIG. 18 corresponds to FIG. 17, but shows the first option for constructing the replicating pinhead tool, in accordance with an embodiment of the present invention.
Figure 19A:
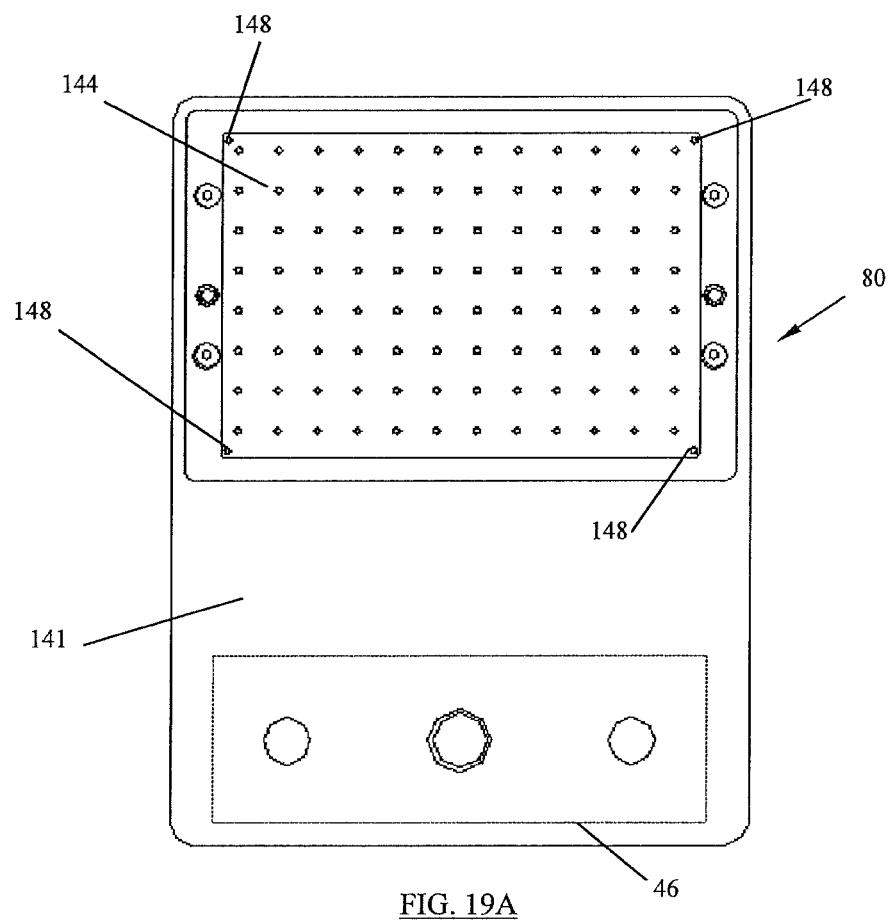
FIG. 19A corresponds to FIG. 17, but shows the top view of a 96-pin replicating tool, in accordance with an embodiment of the present invention.
Figure 19B:
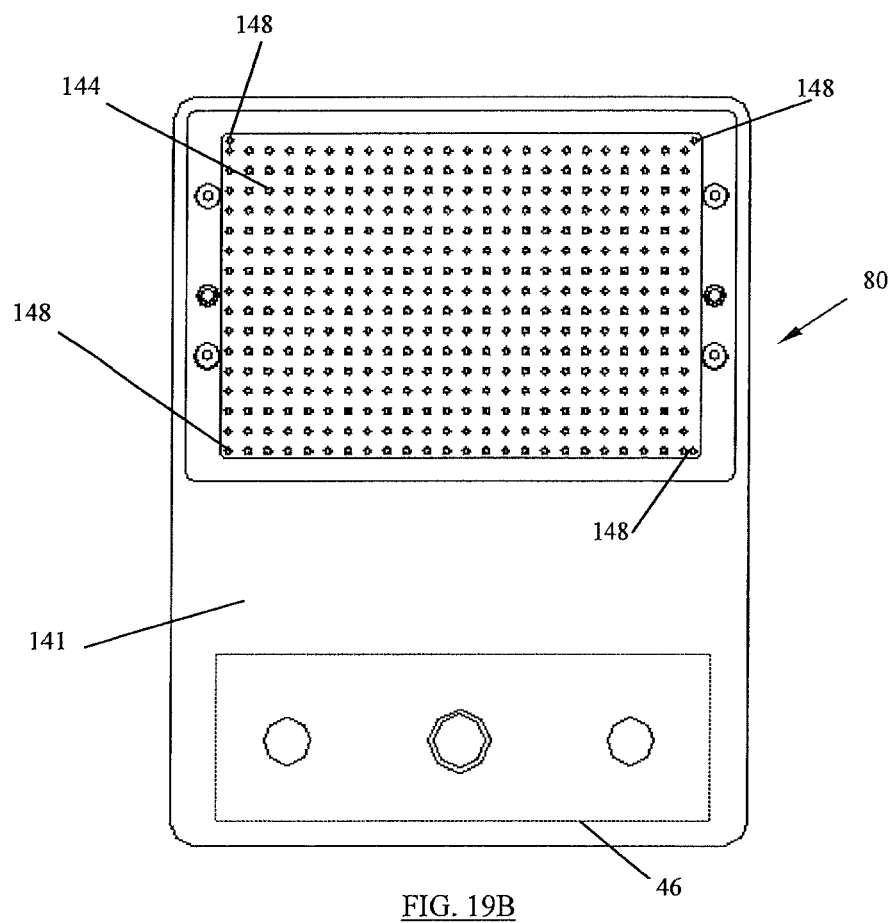
FIG. 19B corresponds to FIG. 17, but shows the top view of a 384-pin replicating tool, in accordance with an embodiment of the present invention.
Figure 19C:
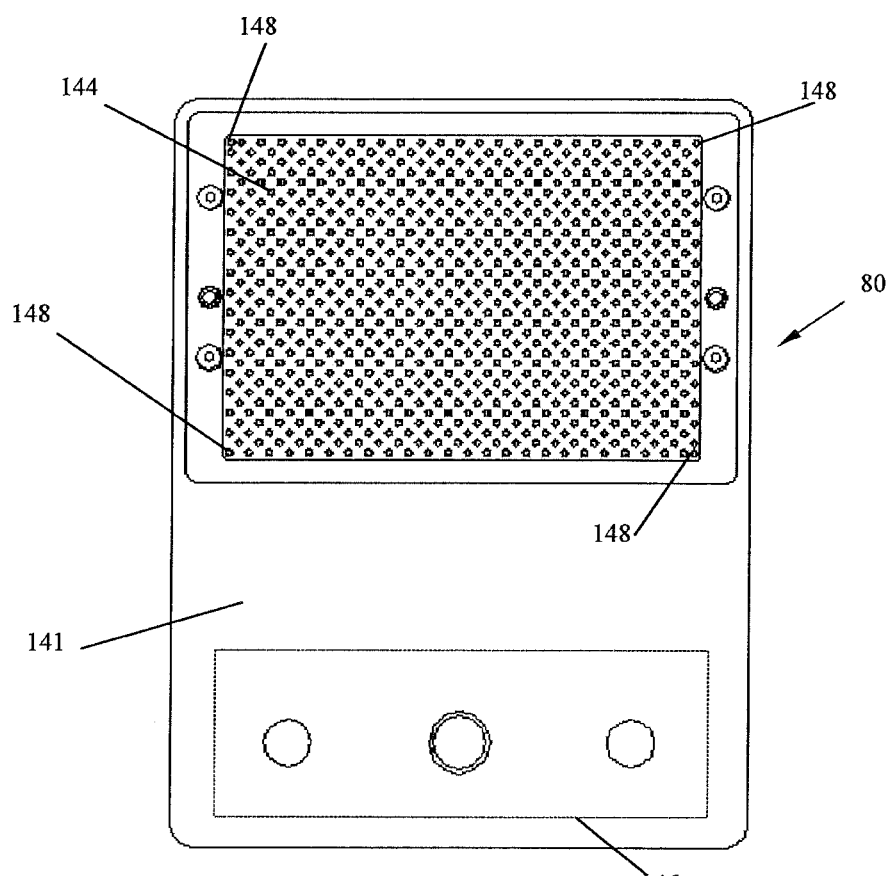
FIG. 19C corresponds to FIG. 17, but shows the top view of a 768-pin replicating tool, in accordance with an embodiment of the present invention.
Figure 19D:
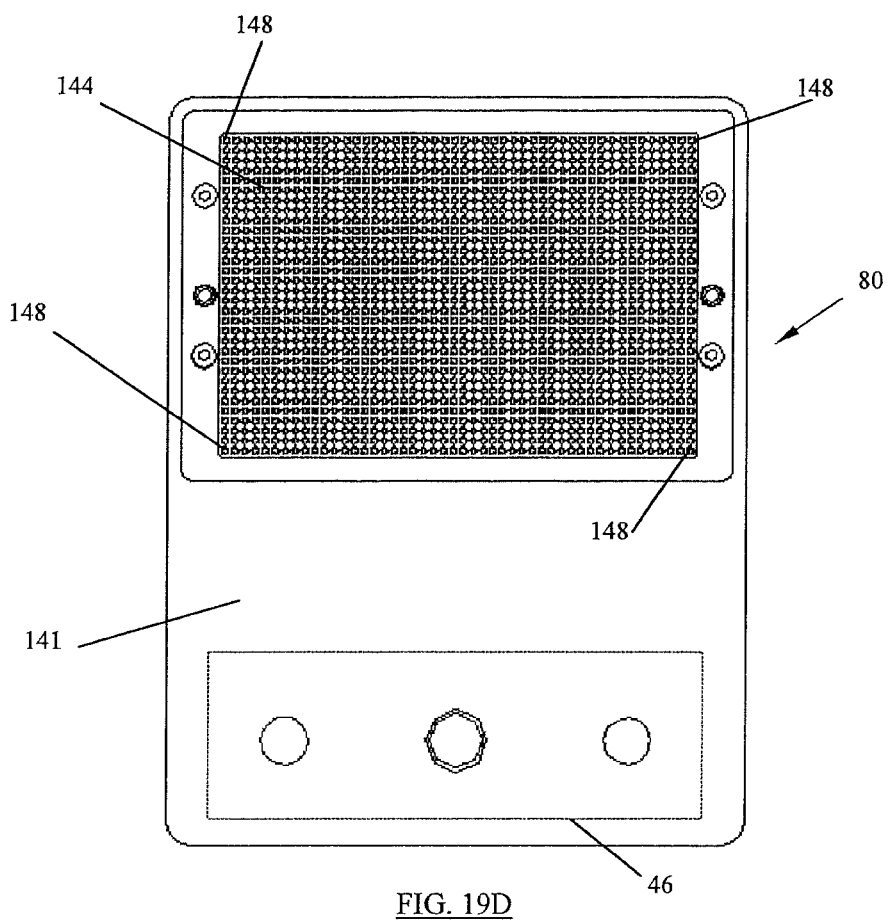
FIG. 19D corresponds to FIG. 17, but shows the top view of a 1536-pin replicating tool, in accordance with an embodiment of the present invention.

Replicating tools with solid pins are not new. Other companies, such as V&P Scientific, have been manufacturing replicating pinheads. However, the existing tools comprise one or two solid metal plate(s) with an array of holes that are precisely drilled into the plate(s). The pins freely float inside the holes. The number of pins and their size varies based on the application. The most commonly used formats of such pinheads include: 96=12×8 pins with 9 mm pin-to-pin distance, 384=24×16 with 4.5 mm pin-to-pin distance, and 1536=48×32 pins with 2.25 mm pin-to-pin distance, as shown in FIGS. 19A, 19B, and 19D respectively. The drawbacks of such pinheads include high cost of production and problems with manufacturability, especially when high-accuracy and high-density pinheads are needed. For example, drilling a large number of very accurate holes in a metal plate can be expensive. Even if one hole is damaged during the machining, the whole plate will be useless. The pins have to slide freely inside the holes (see FIG. 18), but they should not wobble inside the holes. That means the manufacturing tolerances for the pins and holes must be very tight. To minimize wobbling, we may use a thicker plate. However, that makes drilling the holes even more difficult, and would increase the overall weight. Also, if the pins are very thin, for example 0.7 mm or less, drilling accurate holes of that size can be very costly or nearly impossible. Also, this design is limited in terms of the maximum number of pins that can be fit into the specified standard space (around 108 mm by 72 mm).

To overcome such difficulties and minimize the production cost, a new design is disclosed herein. FIG. 18 shows the design of standard-density (i.e., 96, 384, 768, and 1536 formats) pinheads according to embodiments of the present invention. The new design uses tubes or bushings 147 instead of machined holes. One tube 147 is used for each pin 144. Such tubes are produced in different sizes of ID (inside diameter), OD (outside diameter) and variety of lengths and with tight tolerances on the ID or OD. Since such tubes are mass-produced, the cost of each tube is very low. A preferred material for the tubes 147 and pins 144 is stainless steel, but other materials are also possible. The length of the tube can be increased to minimize the wobbling without tightening the tolerance between the pin and the tube. Therefore, the tolerance between the pin 144 and the tube 147 can be loosened to help the pin slide more freely. In one embodiment, two plates 142 are used to maintain a uniform distance between the tubes. In FIG. 18, the base plate 141 constitutes the base for other components. The base plate 141 is typically made of aluminum or other suitable materials and is machined to precise dimensions. The parts 142 are typically made of polymers such as polycarbonate, polystyrene, polypropylene, or similar types. Other materials, for example Delrine, Teflon, Brass, or Aluminum can also be used. The advantage of using polymers is that they can be easily fabricated in large quantities using injection molding. To assure that the two plates 142 will be precisely aligned and parallel with each other, for example four corner tubes 148 can be used. Since those four corner tubes 148 are tightly fit into the four corner holes of the base plate 141, and because the base plate 141 is accurately machined, the four corner tubes 148 will be at proper distance and parallel to each other. A preferred method of assembly would be to make the two parts 142 out of polymers and to lightly press-fit the tubes 147 and 148 into the holes of the two plates 142. In order to simplify the assembly process, the holes can be slightly tapered. As it is shown in FIG. 18, each pin 144 has a head 146 that prevents it from falling down and a tip 145 that can be made thinner than or the same size as the middle part of the pin.

Figure 21:
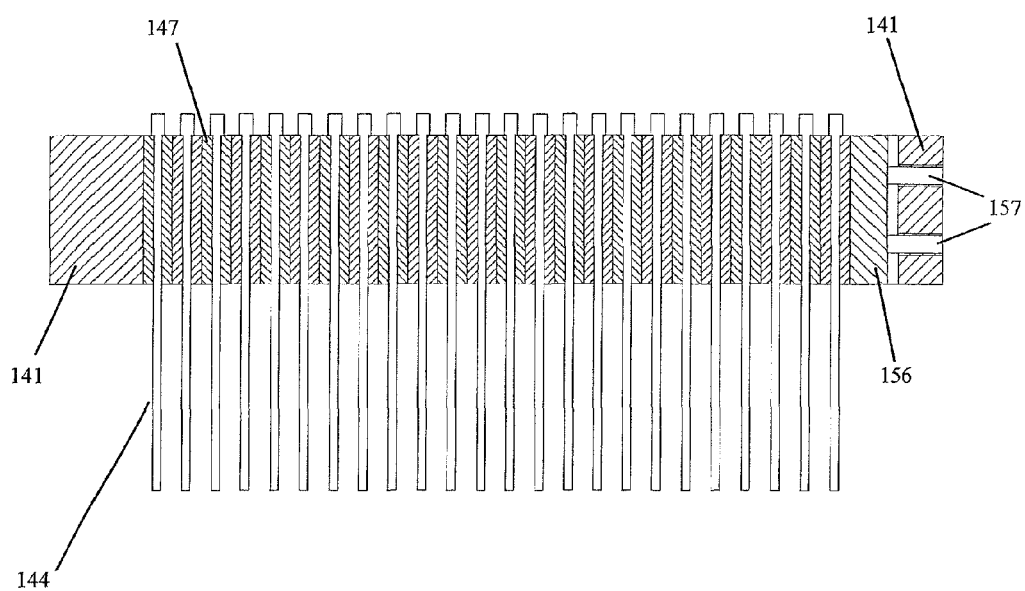
FIG. 21 corresponds to FIG. 17, but shows the second option for constructing the replicating pinhead tool, in accordance with an embodiment of the present invention.

Using the pin and tube method has another important advantage over the traditional pin and drilled-hole method. As illustrated in FIG. 21, tubes can be assembled side-by-side to produce a very high-density pinhead that would have been otherwise nearly impossible or very costly to make with other techniques. In one embodiment, a pusher plate 156 with two setscrews 157 can be used to hold the tubes in place. Other methods can also be used to hold the tubes together. For example one may use epoxy glue to maintain the tubes in place even after removing the fixture.

Figure 8:
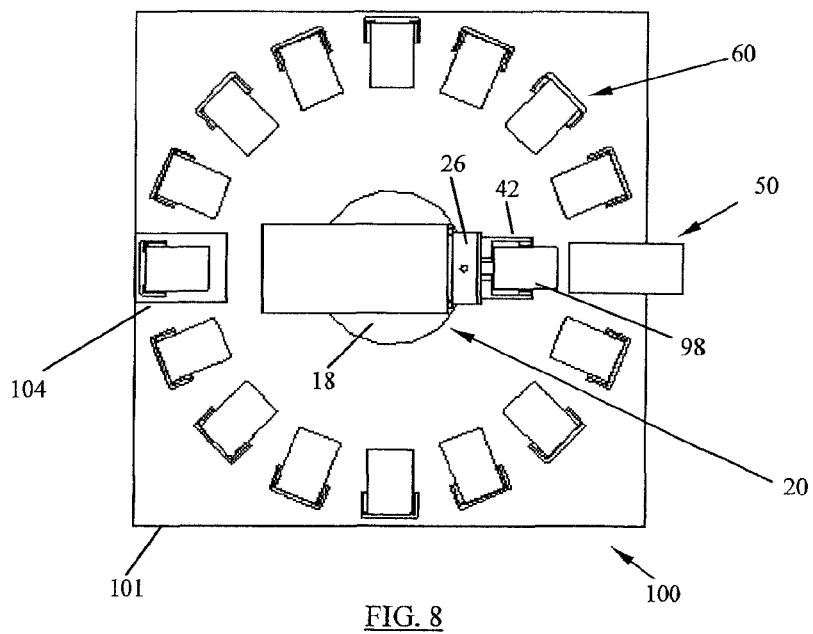
FIG. 8 is a schematic top view of a high-capacity labware stacking device comprising a functional module with a rotary base and a plurality of shelves, in accordance with an embodiment of the present invention.
Figure 9:
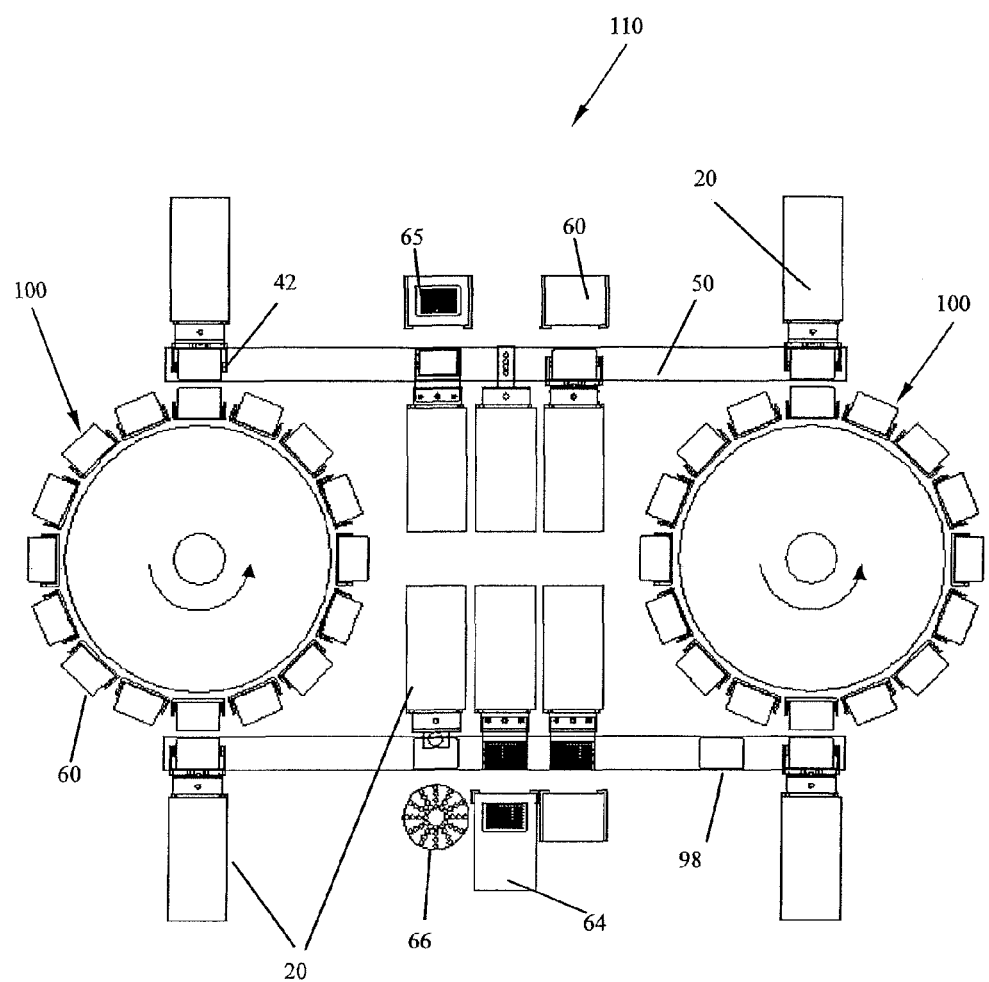
FIG. 9 is a schematic top view of another exemplary configuration of the modular and scalable apparatus for automating a process in accordance with an embodiment of the present invention.
Figure 10:
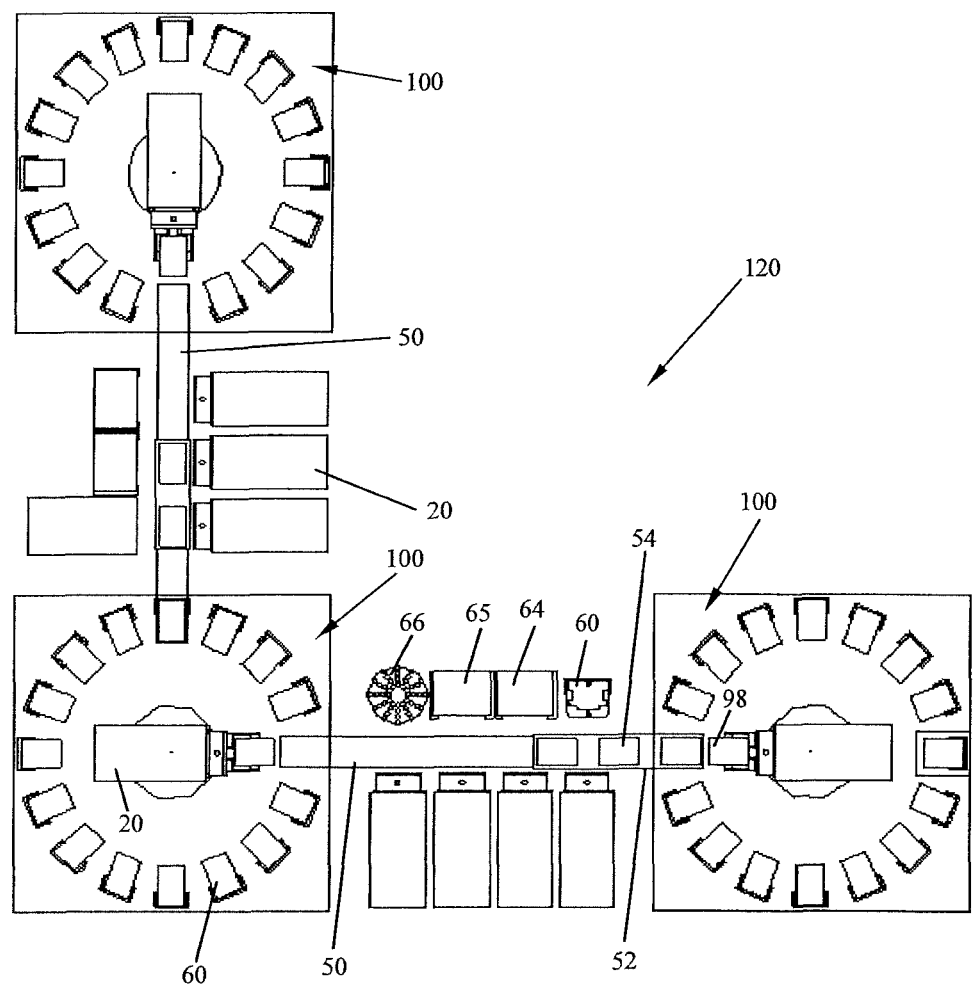
FIG. 10 is a schematic top view of another exemplary configuration of the modular and scalable apparatus for automating a process in accordance with an embodiment of the present invention.

An important feature of an automation system according to embodiments of the present invention is the modularity, scalability, and reconfigurability. This means that the same modules described in the automation system 10 of FIG. 1 or 2 can be re-arranged in different configurations in order to make new machines or automation systems for new applications. FIGS. 8 to 10 show other exemplary configurations of the automation system, in accordance with embodiments of the present invention.

FIG. 8 shows a high-capacity plate stacker machine (hereinafter also referred to as a "hotel") 100 comprising a functional module 20 with a rotary base 18 and a plurality of shelf sub-modules 60, in accordance with an embodiment of the present invention. A gripping tool 42 is used to transfer a labware 98 between the shelves of sub-modules 60 and the tray of conveyer 50. In order to access a specified shelf 60, the functional module 20 rotates on the rotary base 18 such that the gripping tool 42 is oriented right in front of the specified shelf 60. It can be seen that by adding a rotary base 18 to the functional module 20 and by increasing the number of sub-modules 60, one can create a new stacker machine 100 with a significant increase in capacity as compared with the stacker machine 11 in FIG. 1. Another option is to have the functional module fixed and rotate the shelf sub-module assembly, as illustrated in FIG. 9, in accordance with an embodiment of the present invention. A hotel 100 may comprise an enclosure 101 that maintains a controlled environment for the plates with physical or chemical conditions such as temperature, pressure, or humidity that are different from those of the outside environment. One may also use a separate enclosure 104 for each individual shelf sub-module 60 in order to maintain a different environmental condition only for specific sub-module(s).

FIG. 9 is a diagram showing another exemplary configuration 110 of the automation system according to an embodiment of the present invention. The automation system 110 comprises two hotels 100 that provide a high capacity storage space for sample containers 98, a plurality of functional modules 20, a plurality of tools and sub-modules 60, 64, 65, and 66, and two conveyers 50 with a tray that comprise three plate holders 54. The conveyers 50 are used to move sample plates 98 between the hotels 100 and different functional modules 20. The applications of such a system are vast. By changing the tools and sub-modules, different functionalities can be added to the system. For example, by using a 96-format or 384-format pipetting head as a tool, the automation system 110 becomes a high-capacity and high-throughput liquid handling system. By using a replicating tool 80 (see FIG. 1) and a wash-tower sub-module 70 (see FIG. 1), the same system in FIG. 9 becomes a high-capacity cell replicating system. By using two replicating tools 80 and two wash-towers 70 in the same system 110, the throughput can be doubled as compared with the system 10 in FIG. 1. The reason is that when one replicating tool is being washed and sterilized, the second replicating machine can replicate another set of labware.

FIG. 10 is a diagram showing another exemplary configuration 120 of the automation system according to an embodiment of the present invention. An automation system like the one in FIG. 10 can be used to automate very complicated processes, while maintaining a relatively small footprint and a low cost. The cost of the automation system is significantly less than comparable systems, as the core part of the system is made of few relatively simple modules. It not only reduces the development cost and time significantly, but also reduces the production cost due to repetition and reuse of identical or similar components. For example, the machining cost of a component is significantly reduced if a large quantity of that component is produced in one setup. Other advantages are reduced documentation, easier maintenance, and simplified stocking of components. The modularity and scalability of the automation system according to embodiments of the present invention is evident for example from the sequence of configurations presented in FIGS. 2, 8, 9, and 10. It is also evident that such a system can be configured with new tools and sub-modules in order to be used for a plurality of applications. It is to be appreciated that the above configurations related to the present invention are by way of example only. Many other variations on such configurations should be obvious to one or ordinary skill in the art and such obvious variations are within the scope of the present invention.

Figure 22:
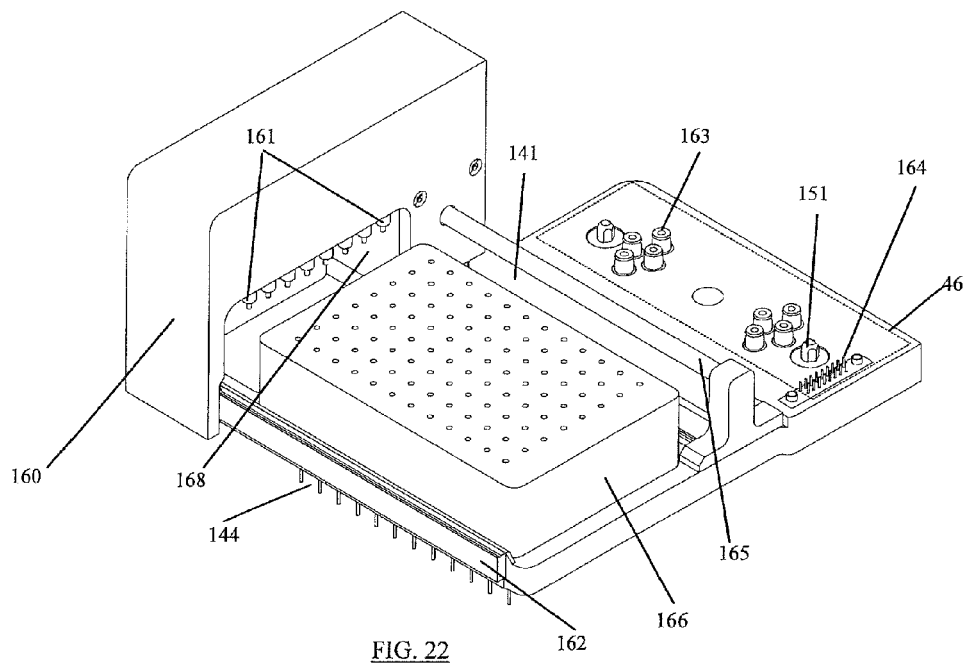
FIG. 22 is a perspective view of a 96-pin re-arraying pinhead tool of the modular apparatus of an embodiment of the present invention.
Figure 23:
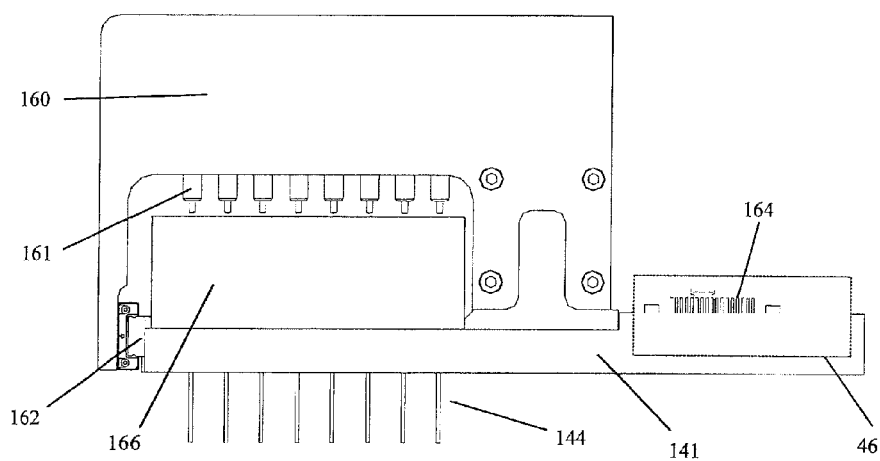
FIG. 23 corresponds to FIG. 22, but shows the side view of a re-arraying tool with 96 separately indexable pins, in accordance with an embodiment of the present invention.

FIG. 22 shows the assembly and components of a Re-arraying tool with ninety-six separately indexable pins, in accordance with an embodiment of the present invention. The tool consists of an actuation mechanism 160 with eight pneumatic or electrical actuators 161. The actuation mechanism 160 moves along the linear bearings (or rails) 162 by means of a motor 168 and a lead screw 165, in order to access different columns of pins. In this exemplary configuration with ninety-six pins, the pins are arranged in a rectangular format with eight rows and twelve columns. When the actuation mechanism aligns with a specified column of pins, any of those eight pins can be actuated separately or simultaneously by the corresponding actuator(s) 161. FIG. 23 shows one column of pins 144 and the actuators 161 from the side view, in accordance with an embodiment of the present invention. FIG. 22 shows the tool's attachment site 46 with two locating pins 151, one electrical connector 164, and eight pneumatic fittings 163, in accordance with an embodiment of the present invention. The attachment site is used to connect the tool to the general purpose tool interface 29 (see FIG. 6) of a functional module. When the tool is attached to the tool interface, the electrical connector 164 and pneumatic fittings 163 of the tool will connect to the corresponding connector and fittings of the tool interface 29 of the functional module, which provides the electrical and pneumatic power required for actuating the motor 168 and actuators 161 of the tool. This provides a high degree of modularity and functionality, as the re-arraying tool can be easily detached from a functional module and replaced by another tool, e.g., a replicating pinhead tool 80, and therefore the same functional module can be used for multiple applications.

Figure 24:
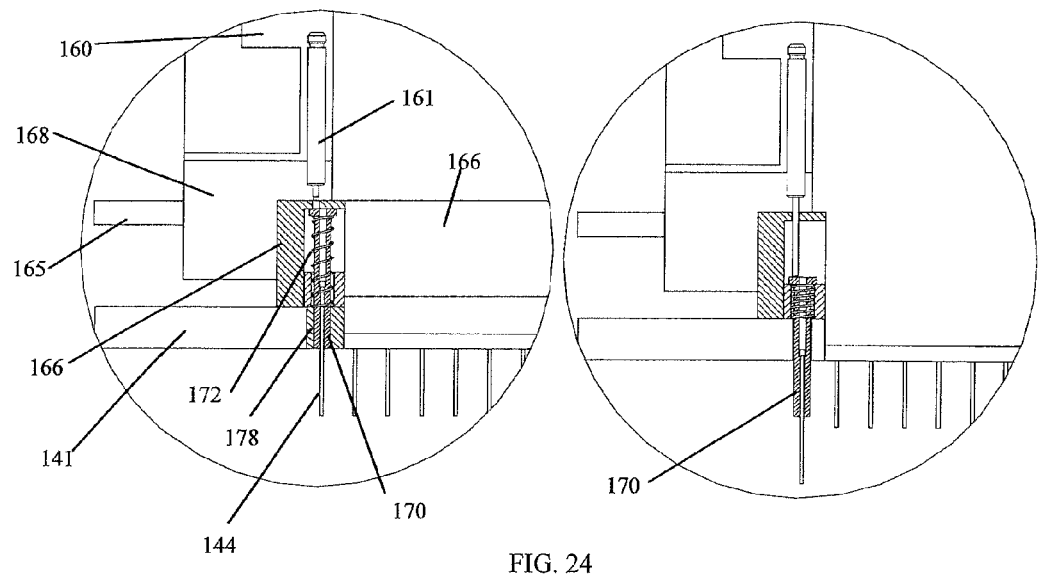
FIG. 24 corresponds to FIG. 22, but shows the cross-section of one exemplary pin with its guiding and actuation mechanism, in accordance with an embodiment of the present invention.
Figure 25:
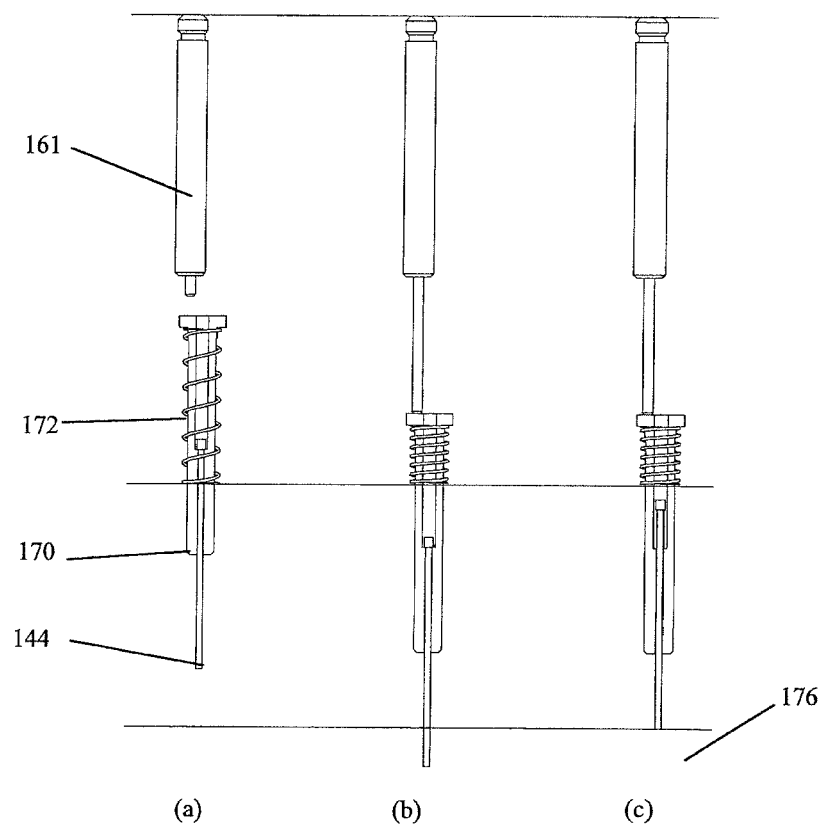
FIG. 25 corresponds to FIG. 24, but shows the cross-section of one exemplary pin with its actuation mechanism during the operation, in accordance with an embodiment of the present invention.

FIG. 24 illustrates the guiding and actuation mechanisms for each pin 144, in accordance with an embodiment of the present invention. The pin 144 can float freely and precisely inside a bushing 170. The bushing 170 also slides up/down in a precise hole 178 on the base plate of the tool. When the actuator 161 is not activated (left figure), the pin and its bushing are moved up by means of a spring 172. The Cover plate 166 limits the upward movement of the bushing 170. When the actuator 161 is activated (right figure), it pushes the bushing 170 and the inside pin 144 down against the spring 172. FIG. 25 illustrates the operating sequence of a pin. When the actuator 161 is not activated (FIG. 25*a*), the bushing 170 and the pin 144 are held up by means of a spring 172. This represents the normal state of the ninety-six pins. When one pin has to move down to pick up or transfer a sample, the corresponding actuator 161 is activated (FIG. 25*b*) and moves the bushing 170 and the pin 144 all the way down. If the pin 144 touches a solid work-surface 176 (FIG. 25*c*), it will float up inside the bushing 170 and does not damage the sample or the work-surface. This is a unique and important feature of the re-arrayer device as disclosed herein. Furthermore, and as should be obvious to one of ordinary skill in the art, such floating pins can be used in a re-arrayer that does not comprise a moving actuation mechanism 160, for example in a re-arrayer that comprises a conventional actuation mechanism.

The re-arraying tool in FIG. 22 can be used for picking randomly distributed samples on a work-surface and transferring them in a standard 96-format rectangular array. In applications related to biology research, the samples are typically biological samples such as bacteria colonies or Yeast cell colonies that are grown on a growth media, e.g., an agar surface.

While certain exemplary embodiments have been described and shown in the accompanying drawings, it is to be understood that such embodiments are merely illustrative and not restrictive of the broad invention and that this invention is not limited to the specific constructions and arrangements shown and described, since various other modifications may occur to those ordinarily skilled in the art upon studying this disclosure. In an area of technology such as this, where growth is fast and further advancements are not easily foreseen, the disclosed embodiments may be readily modifiable in arrangement and detail as facilitated by enabling technological advancements without departing from the principals of the present disclosure or the scope of the accompanying claims.

The invention claimed is:

1. An apparatus, comprising:
    a plurality of bushings arranged and held together in an array; and
    a plurality of pins residing in the plurality of bushings, the plurality of pins for transferring samples;
    wherein each bushing has opposing open ends, and the pin residing in the bushing has a length such that a first pin end of the pin can extend through and beyond one of the open ends of the bushing so that the first pin end can contact a sample for transfer,
    and further wherein manufacturing tolerances for inside diameters of the bushings and outside diameters of the pins substantially match, thereby allowing the pins to slide freely within the bushings.

2. The apparatus of claim 1, further comprising one or more plates comprising a plurality of holes in which the plurality of bushings reside and whereby the plurality of bushings are held together in the array.

3. The apparatus of claim 1, wherein each pin is sized so that when the first pin end extends through and beyond on of the open ends, a second free end of the pin opposite the first pin end is within the bushing and spaced from the other open end of the bushing.

4. The apparatus of claim 1, wherein each bushing has a bore terminating in the open end that the pin extends from for sample contact and transfer, and manufacturing tolerance for an inside diameter of each bore that the pin moves in and a manufacturing tolerance for the outside diameter of each pin along a length of the pin that moves in the bore of the bushing substantially match, thereby allowing the pins to slide freely within the bushings.

\* \* \* \* \*